(12) United States Patent
Akingba

(10) Patent No.: US 8,652,084 B2
(45) Date of Patent: Feb. 18, 2014

(54) ARTERIOVENOUS SHUNT WITH INTEGRATED SURVEILLANCE SYSTEM

(75) Inventor: Ajibola George Akingba, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 45 days.

(21) Appl. No.: 13/294,890

(22) Filed: Nov. 11, 2011

(65) Prior Publication Data

US 2012/0059305 A1 Mar. 8, 2012

Related U.S. Application Data

(63) Continuation-in-part of application No. 12/189,669, filed on Aug. 11, 2008, now Pat. No. 8,057,421.

(60) Provisional application No. 60/954,910, filed on Aug. 9, 2007.

(51) Int. Cl.
*A61M 5/00* (2006.01)
(52) U.S. Cl.
USPC .................................. 604/9; 604/8; 604/264
(58) Field of Classification Search
USPC .......................................... 604/8, 9, 507, 264
See application file for complete search history.

(56) References Cited

U.S. PATENT DOCUMENTS

| | | | |
|---|---|---|---|
| 4,397,335 A | 8/1983 | Doblar et al. | |
| 5,094,246 A | 3/1992 | Rusz et al. | |
| 5,873,837 A * | 2/1999 | Lieber et al. | 600/504 |
| 6,663,590 B2 | 12/2003 | Blatter | |
| 7,025,741 B2 * | 4/2006 | Cull | 604/9 |
| 7,566,317 B1 | 7/2009 | Batiste et al. | |
| 2005/0038396 A1 | 2/2005 | Claude et al. | |
| 2005/0107733 A1 | 5/2005 | Faul et al. | |
| 2005/0119602 A1 | 6/2005 | Murphy et al. | |
| 2006/0064159 A1 * | 3/2006 | Porter et al. | 623/1.24 |
| 2006/0190022 A1 | 8/2006 | Beyar et al. | |
| 2006/0204532 A1 * | 9/2006 | John | 424/422 |
| 2006/0224100 A1 | 10/2006 | Gertner | |

OTHER PUBLICATIONS

International Search Report, mailed Nov. 10, 2008, issued in related International patent application No. PCT/US08/72828, filed Aug. 11, 2008.

* cited by examiner

*Primary Examiner* — Leslie Deak
(74) *Attorney, Agent, or Firm* — Law Offices of Grady L. White, LLC

(57) ABSTRACT

A hemodialytic angioacess device for implantation in dialysis patients, comprising an arteriovenous (AV) shunt, anastomotic valves that connect the AV shunt to blood vessels, a valve control system and an integrated surveillance system that measures flow conditions in the blood vessels at the AV shunt, preferably when the valves are closed and the patient is not undergoing dialysis treatment. The flow condition data, which may include data representing the flow rate, pressure, volume and velocity of blood flowing through the vessels, is stored in a memory and transmitted to a health care provider or technician on demand. The data can be used to calculate and monitor important physiological parameters, such as compliance and resistance, for the blood vessels, and help detect and identify dangerous conditions, such as turbulence and stasis, which can contribute to AV shunt failure, vessel injury and other serious complications for the patient.

22 Claims, 12 Drawing Sheets

FIG. 4A – Closed Position
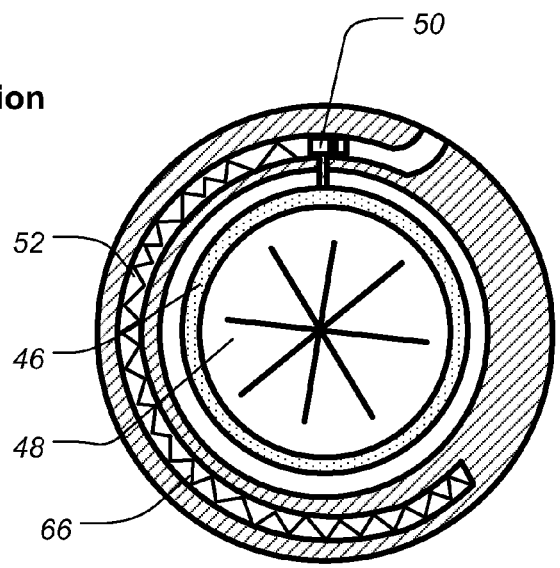
FIG. 4B – Half Open Position
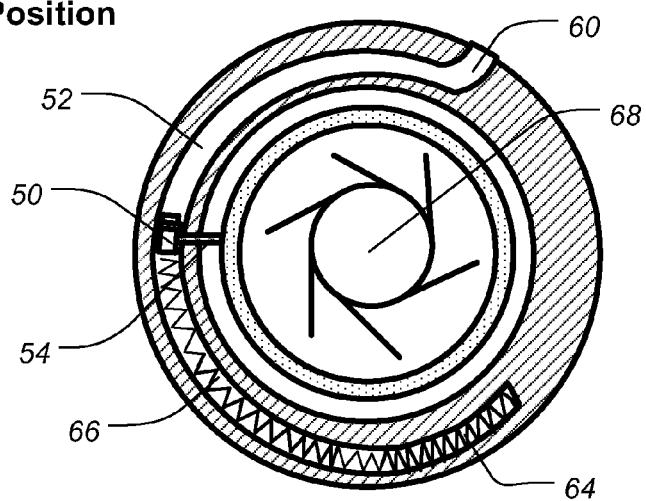
FIG. 4C – Fully Open Position
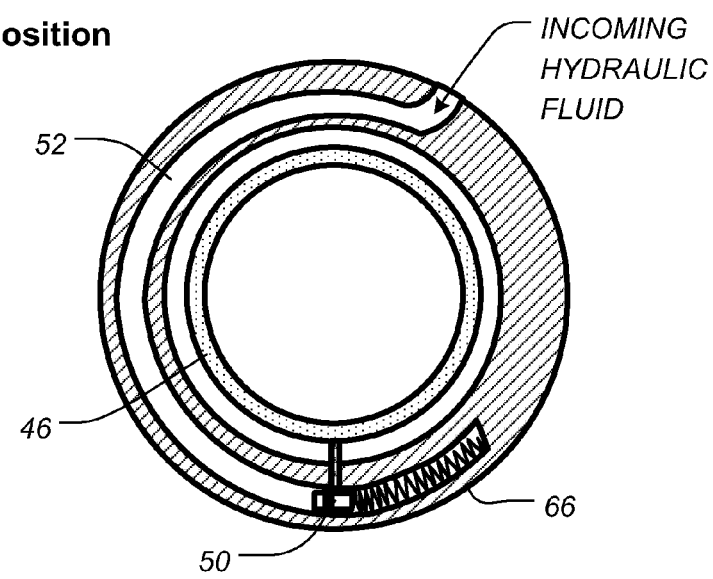

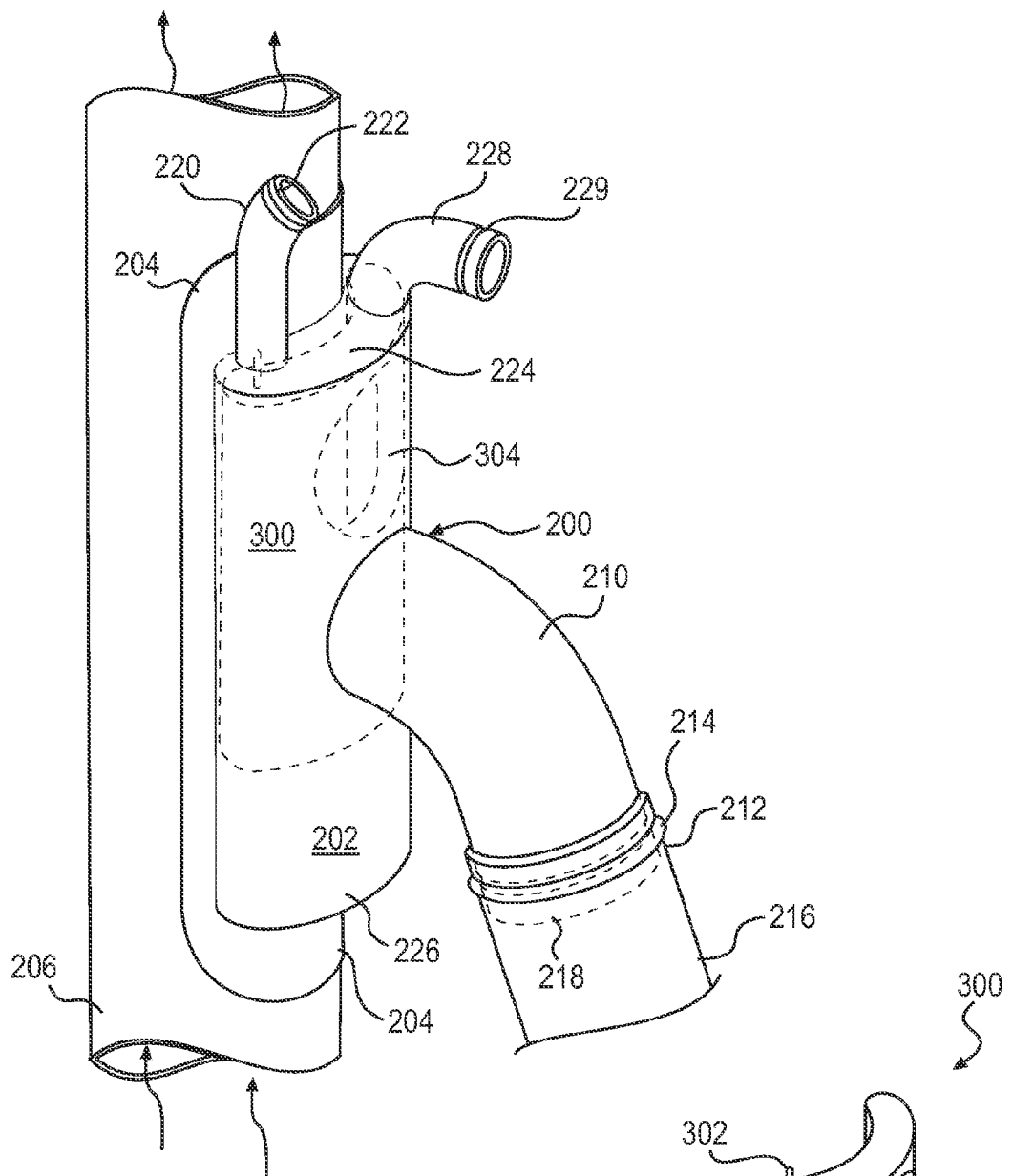
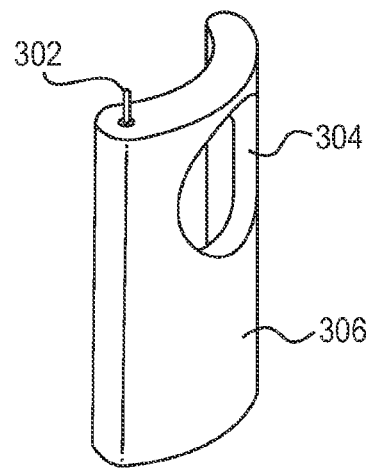
FIG. 8
FIG. 9

ARTERIOVENOUS SHUNT WITH INTEGRATED SURVEILLANCE SYSTEM

CROSS-REFERENCE TO RELATED APPLICATIONS

This application is a continuation-in-part of U.S. application Ser. No. 12/189,669 (now U.S. Pat. No. 8,057,421), filed on Aug. 11, 2008, and claims the benefit of U.S. Provisional Application No. 60/954,910, filed on Aug. 9, 2007. application Ser. No. 12/189,669 and 60/954,910 are both incorporated into this application in their entirety by this reference.

FIELD OF ART

The present invention relates generally to devices and methods for performing hemodialysis for patients suffering from end-stage renal disease (ESRD). More particularly, the invention relates to implantable modular arteriovenous shunt systems, hemodialytic angioacess devices, a anastomotic valves for a hemodialytic angioacess devices, surveillance systems for a hemodialytic angioacess devices, and methods of using same for establishing hemodialytic angioaccess in hemodialysis patients.

RELATED ART

Hemodialysis is a method of removing waste products, such as potassium and urea, as well as free water, from the blood when the kidneys are incapable of adequately performing this function on their own (a condition known as end-stage renal failure). In a typical hemodialysis session, two hypodermic needles are inserted into the patient's body. One needle draws untreated blood from the patient's vascular system and conveys it to an extracorporeal hemodialysis machine for cleansing, while the second needle carries the treated blood from the hemodialysis machine back into the patient's vascular system. For some hemodialysis patients, it may be necessary to undergo these sessions three or more times per week until the failing kidney(s) can be repaired or replaced, or sometimes for the rest of the patient's life. Over time, repeated insertion and removal of needles into the patient's arteries and veins weaken the vessel walls and produce a significant risk of developing infections and aneurysms (large bulges in the vessel walls).

To mitigate or avoid these risks, current practices for providing hemodialysis treatment include implanting an autogenous arteriovenous fistula or synthetic arteriovenous graft, also called an "AV shunt." An AV shunt is an artificial vessel or tube used to join an artery to a vein in such a way that blood flows out of an artery, through the AV shunt and then back into a vein. Although the AV shunt is implanted below the surface of the skin, hemodialysis technicians gain access to the blood flowing through the AV shunt by piercing the skin and the AV shunt with the hypodermic needles, instead of piercing the patient's natural arteries and veins. Thus, untreated blood flowing from a patient's artery into the AV shunt is drawn out of the AV shunt via one hypodermic needle inserted near the arterial end of the AV shunt, and the treated blood is returned to the body via another hypodermic needle that is inserted near the venous end of the AV shunt. As the cleansed blood flowing from the hemodialysis machine is returned to the venous end of the AV shunt via the second hypodermic needle, it flows into the patient's vein, which carries the blood back into the patient's general circulatory system. The advantage of using an AV shunt is that it avoids, or at least reduces, the trauma and damage that would otherwise occur to the patient's natural blood vessels. Depending on the length of the AV shunt, it also provides a larger surface area for accessing the flow of blood, which permits hemodialysis technicians to pierce the patient's body using a more dispersed insertion pattern, thereby reducing the risk and incidence of infection and scarring of the dermal and epidermal layers of the patient's skin.

Unfortunately, there are a number of problems associated with using conventional AV shunts. It has been observed, for example, that implantable AV shunts often fail. Pathological study of the proximal veins of failed AV shunts has revealed a large incidence of myointimal hyperplasia secondary to vessel injury from turbulence, compliance mismatch between shunt material and vein, and mechanical stimulation of perivascular tissues at the anastomosis graft and vessel. Normal blood flow is laminar, with the cellular elements flowing centrally in the vessel lumen, separated from the endothelium by a slower moving clear zone of plasma. Turbulence and stasis caused by the blood flowing into the vein from the AV shunt contribute to clot formation by disrupting laminar flow and bringing platelets into contact with the endothelium, preventing dilution of activated clotting factors from fresh flowing blood, retarding the inflow of clotting factor inhibitors (thus permitting the build up of thrombi) and promoting endothelial cell activation. This situation predisposes the patient to local thrombosis, leukocyte adhesion, and a variety of other endothelial cell effects. Other reasons for shunt failure include recurrent shunt stenosis, infection, pseudoaneurysms and steal syndrome.

When complications associated with implanted AV shunts, such as myointimal hyperplasia, thrombosis, shunt stenosis and clotting, arise and go undetected for a significant period of time, the AV shunt can fail without warning, resulting in potentially devastating consequences. These complications may sometimes be detected in a medical facility while the patient is undergoing dialysis or being treated or examined by a medical professional. The complications also might be detected while the patient is hooked up to complicated and expensive external medical machines and equipment that are designed to monitor and/or test the patient for signs of complications. Prior to the present invention, however, there has been no AV shunt device introduced that has the capacity to monitor and report its own patency data. Consequently, the frequency and unpredictable timing of AV shunt failures and the emergency salvage procedures required to restore their patency (e.g., thrombectomy, angioplasty or revision) presents enormous health, safety and logistical challenges for the patient, surgeon, operating room and dialysis centers.

U.S. Pat. No. 7,025,741 issued to Cull, which is hereby incorporated herein in its entirety by this reference, discloses an implantable arteriovenous graft system that the inventor claims eliminates or at least reduces arterial steal and thrombosis by providing an arteriovenous graft (shunt) having at one or both ends a valve device comprising an inflatable balloon or a magnetically-activated piston which, when activated, constricts the graft to partially or entirely prevent the flow of blood while the patient is not undergoing dialysis treatment. In order to determine whether the device is effective in eliminating or reducing arterial steal, however, Cull suggests monitoring the patient's condition over a period of time, such as days or weeks, while selectively opening and closing the valve until arterial steal is minimized. Thus, Cull's device has no ability to monitor itself, or to store and report its own patency data (e.g., flow data near the arterial end of the graft indicating the existence of arterial steal), which may increase the risk that arterial steal might go undetected for a longer period of time. As a result, the patient must be monitored for symptoms of arterial steal. Moreover, because Cull's device comprises a single graft (shunt) with valves at one or both ends, a vascular surgeon using Cull's device has little or no ability during surgery to shorten the overall length of the device (e.g., by cutting pieces off one or both ends of the graft) or extending the overall length of the device (e.g., by inserting additional or longer pieces of graft material between the valves) in order to construct a device that has the optimal overall length and arrangement for the particular patient and/or implantation site.

Accordingly, there is a need for an implantable AV shunt device capable of monitoring and storing data concerning its own patency, even when the patient is not at a medical facility, and further capable of transmitting the stored patency data to an external medical device, medical technician or other medical professional for further processing and analysis upon demand. There also is a need for an implantable AV shunt device that may be adjusted and/or resized by the vascular surgeon during the implantation procedure to provide a custom fit for the patient, regardless of the patient's size or the geometry of the implantation site, using surgical techniques that most vascular surgeons are already very familiar and comfortable with performing.

SUMMARY OF INVENTION

The present invention addresses these needs by providing an implantable modular AV shunt device, which is capable of monitoring and reporting its own patency. One embodiment comprises a plurality of modular components that may be assembled and adjusted by the vascular surgeon during the implantation procedure, using well-known surgical techniques, in order to provide a custom fit and arrangement. In this embodiment, the device comprises an arterial anastomotic valve that permits blood flowing through an artery to pass into the shunt device, a venous anastomotic valve that permits blood flowing through the shunt device to pass into a vein, a medial flow control unit, a first flexible shunt that carries blood from the arterial anastomotic valve to the medial flow control unit, a second flexible shunt that carries blood from the medial flow control unit to the venous anastomotic valve, and a valve control system. The medial flow control unit is operable with the valve control system to independently control both the rate at which blood is permitted to enter the shunt device via the arterial anastomotic valve, as well as the rate at which blood is permitted to exit the shunt device via the venous anastomotic valve.

A variety of different types of anastomotic valves may be used in embodiments of the present invention. In one embodiment, the medial flow control unit is operable to control the diameter of iris-like apertures in the valves, which apertures are formed by the walls of cylindrically-shaped sleeves fixedly attached to static and rotating rings located in the arterial and venous anastomotic valves. When a dialysis treatment is to begin, the valve control system is activated to cause the diameter of the apertures to expand, thereby permitting blood to flow from the artery into and through the arterial anastomotic valve, through the first flexible shunt interposed between the arterial anastomotic valve and the medial flow control unit, through the medial flow control unit, through the second flexible shunt interposed between the medial flow control unit and the venous anastomotic valve, into the venous anastomotic valve, and then out of the device and into the vein. Hypodermic needles, which are attached to the dialysis machine, are inserted into the first and second flexible shunts in order to draw blood out of the modular shunt device for cleansing and to return the cleansed blood to the patient's vascular system. When the dialysis treatment is finished and the hypodermic needles are removed from the first and second flexible shunts, the valve control system is activated again to contract the diameter of the apertures, thereby preventing blood from continuing to flow into the modular shunt device. Biasing means within the valves keep the valves closed until it is time for the next dialysis session, whereupon the valve control system is reactivated to open and close the valves again.

In another embodiment, shuttle valves may be employed at the anastomosis of the shunt with the blood vessels. Each shuttle valve comprises a valve housing, a skirt for surgically attaching the valve housing to an opening over a blood vessel, an orifice on the side of the valve housing facing the opening in the blood vessel, a shunt connector for attaching and fluidly coupling an AV shunt to the valve housing opposite the blood vessel, and a stopper, movably disposed in the valve housing such that, responsive to operation of a valve control system, the stopper "shuttles" back and forth inside the valve housing in order to alternatively block and unblock the orifice, thereby closing and opening shuttle valve). One end of the stopper in the shuttle valve has an aperture that, when the stopper is moved into the open position, the aperture in the stopper is aligned with the orifice in the valve housing to allow fluid in the blood vessel to pass out of the blood vessel and then into and through the orifice, the aperture, the valve housing, the shunt connector and AV shunt. The other end of the stopper comprises an apron that, when the valve is in the closed position, blocks or obstructs the orifice in the valve housing so as to prevent fluid in the blood vessel from passing through orifice.

One shuttle valve is located at the arterial anastomosis and another shuttle valve is located at the venous anastomosis. When a dialysis session is about to begin, the valve control system is activated to move the stoppers in both shuttle valves to their open positions, thereby allowing blood flowing in the artery to pass into and flow through the AV shunt, so that it may be drawn out of the patient's body via a first hypodermic needle inserted near the arterial end of the AV shunt, cleansed, and returned to the patient's body via a second hypodermic needle inserted in the venous end of the AV shunt. When the dialysis session ends, the valve control system may be activated again (or deactivated, as the case may be) to cause the stoppers to shuttle back to their closed positions, thereby preventing fluid flowing through the artery from entering the shuttle valve and passing into the shunt. As will be described and shown in more below, the shuttle valves may also include springs, or other suitable devices, which are configured to bias the stoppers toward their closed positions in the valve housing so that the shuttle valves will remain closed while no dialysis treatment is currently underway and the patient is away from the medical facility.

Embodiments of the present invention include an integrated surveillance system configured to collect data representing quantitative measurements characterizing the flow of blood through the vessels at the arterial and venous anastomotic valves. More specifically, the arterial and venous anastomotic valves are equipped with one or more flow sensors that are electrically coupled to a microprocessor in the medial flow control unit via insulated electrical leads. In some embodiments, the insulated electrical leads may be embedded in flexible fluid tubes, interposed between the two anastomotic valves and the medial flow control unit, which carry hydraulic fluid used to provide the mechanical force required to open and/or close the valves. In other embodiments, the insulated electrical leads are independent from the flexible fluid (hydraulic) tubes. In any case, the electrical leads provide electrical connectivity between the flow sensors and the medial flow control unit, which enables transmission of electrical signals representing the values generated from the quantitative measurements, such as pressure, volume and speed values for the blood flowing through the vessels at or near the anastomotic valves.

As discussed below, the medial flow control unit houses a printed circuit board containing one or more microprocessors, memory modules, transceivers and batteries, which operate to collect, store and wirelessly transmit the measured blood flow condition data to an external receiver for further processing and analysis by other medical devices, medical professionals and/or dialysis technicians.

In another aspect of the invention, there is provided a method for establishing hemodialytic angioacess, comprising (1) attaching an arterial anastomotic valve to an artery, the arterial anastomotic valve comprising a first static ring, a first rotating ring, and an arterial aperture formed by a first sleeve interposed between the first static ring and the first rotating ring; (2) attaching a venous anastomotic valve to a vein, the venous anastomotic valve comprising a second static ring, a second rotating ring, and a venous aperture formed by a second sleeve interposed between the second static ring and the second rotating ring; (3) providing a medial flow control unit; (4) installing a first flexible shunt between the medial flow control unit and the arterial anastomotic valve; (5) installing a second flexible shunt between the medial flow control unit and the venous anastomotic valve; and (6) rotating the first and second rotating rings in a first direction to cause the first and second sleeves to untwist, thereby expanding the arterial and venous apertures to increase the rate at which blood is permitted to flow through the arterial and venous anastomotic valves. The method may further include: (7) rotating the first and second rotating rings in the opposite direction to cause the first and second sleeves to twist, thereby contracting the arterial and venous apertures to reduce the rate at which blood is permitted to flow through the arterial and venous anastomotic valves. Typically, rotating the first and second rotating rings is accomplished by injecting hydraulic fluid into a fluid injection port attached to the medial flow control unit, thereby forcing the hydraulic fluid into the first and second hydraulic fluid tubes and the arterial and venous anastomotic valves, which in turn forces the first and second rotating rings to rotate in the direction that expands the arterial and venous apertures to permit a higher rate of flow.

In yet another aspect of the invention there is provided a hemodialytic angioacess device for implantation in dialysis patients, comprising an AV shunt, anastomotic valves that connect the AV shunt to blood vessels, a valve control system and an integrated surveillance system that measures flow conditions in the blood vessels in the vicinity of the AV shunt. In some embodiments, data describing the flow conditions through the blood vessels may be collected and stored while the anastomotic valves are closed and the patient is not undergoing dialysis treatment. In other embodiments, the data may be collected and stored while the anastomotic valves are open. In still other embodiments, the data may be collected and stored while the anastomotic valves are open, as well as while the anastomotic valves are closed. The flow condition data, which may include data representing the velocity, pressure and volume of blood flowing through the vessels, is stored in a memory storage area in the device, and transmitted to a health care provider or technician on demand in response to a wired or wireless signal transmitted to the implanted hemodialytic angioaccess device from an external transmitter. Once extracted and transmitted, the data can be used, for example, to calculate compliance and resistance characteristics for the blood vessels, and help detect and identify dangerous conditions, such as turbulence and stasis, which contribute to AV shunt failure, vessel injury and other serious complications for the patient.

In still another aspect of the invention, there is provided an integrated surveillance system for an implantable arteriovenous shunt, comprising a control unit having a microprocessor and a memory storage device, an anastomotic valve for surgically connecting the arteriovenous shunt to a blood vessel, a flow sensor, and an electrical lead. The flow sensor is attached to the anastomotic valve so that, after the anastomotic valve is surgically attached to the blood vessel, the flow sensor will be in contact with fluid flowing through the blood vessel. The flow sensor is configured to collect data describing flow conditions in the blood vessel, such as pressure, volume and speed of the fluid. The microprocessor in the control unit is preprogrammed to cause the data collected by the flow sensor to be transmitted to the control unit via the electrical lead, where the data is then stored in the memory storage device for later extraction.

Multiple flow sensors may be employed, if desired or necessary, in any of the above-described aspects and embodiments of the invention, in order to provide simultaneous and/or continuous collection of flow condition data in both the vein and the artery while the anastomotic valves are closed, as well as while the anastomotic valves are open.

BRIEF DESCRIPTION OF THE DRAWINGS

The present invention and various aspects, features and advantages thereof are explained in detail below with reference to exemplary, and therefore non-limiting, embodiments with the aid of the drawings, which constitute a part of this specification and include depictions of the exemplary embodiments. In these drawings:

FIGS. 4A, 4B, and 4C show, respectively, cross-sectional views of the venous anastomotic valve in the closed, half open and fully-open positions.

FIG. 8 shows an exemplary embodiment of a shuttle valve for hemodialytic angioaccess according to an embodiment of the invention.

FIG. 9 shows an exemplary embodiment of a stopper for the shuttle valve illustrated in FIG. 8.

DETAILED DESCRIPTION OF EXEMPLARY EMBODIMENTS

Figure 1:
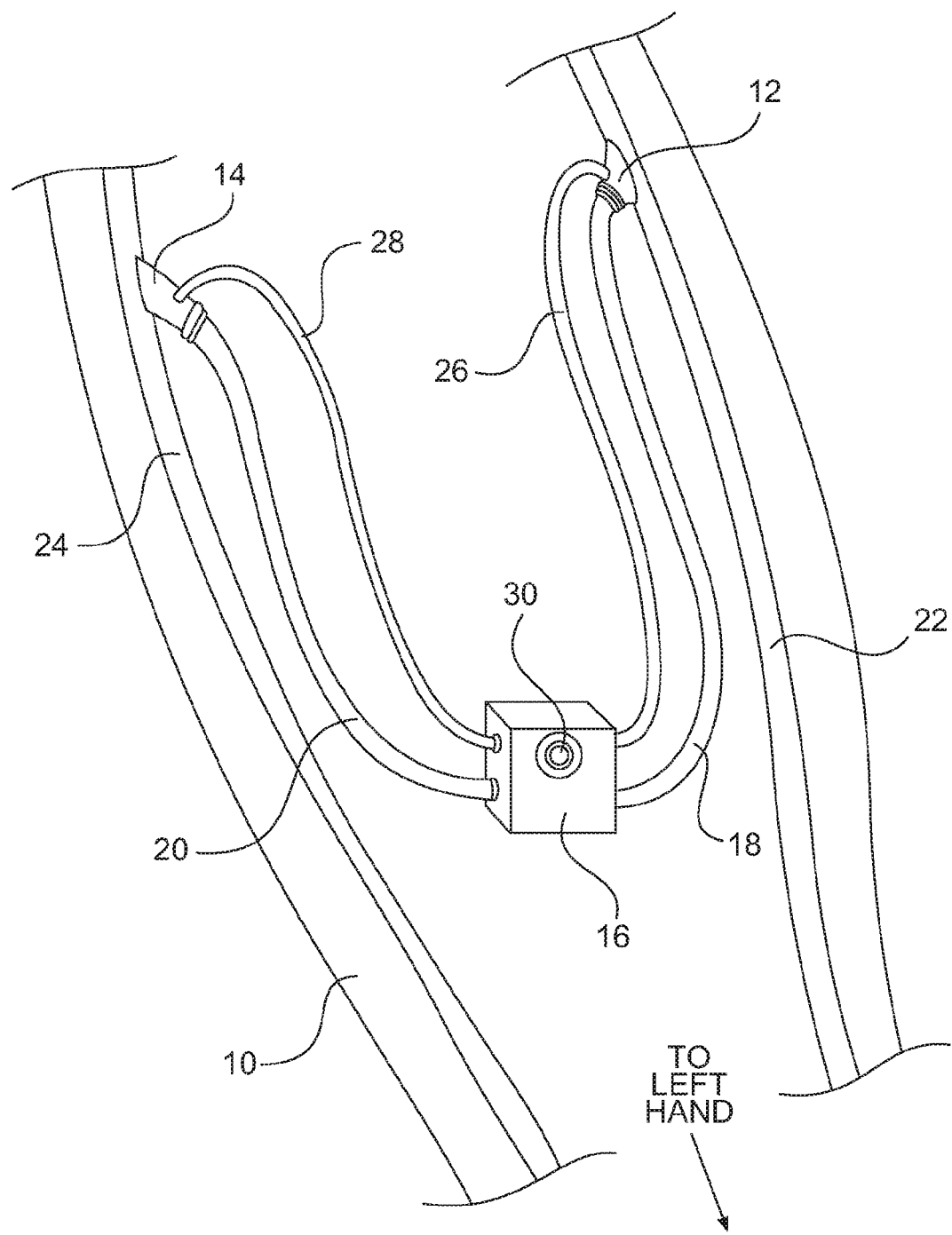
FIG. 1 shows an exemplary embodiment of a modular arteriovenous shunt device according to the present invention.

The present invention provides an arteriovenous shunt device for establishing hemodialytic angioaccess. Devices operating according to a preferred embodiment of the present invention are capable of collecting and storing data concerning its own patency, and transmitting the data to an external receiver for further processing and analysis by medical technicians or practitioners. Some embodiments of the present invention have a modular design that includes at least two flexible shunts and one medial flow control unit. In embodiments having the modular design, the medial flow control unit is relatively easily connected between the two flexible shunts by the vascular surgeon during the implantation procedure. Because this embodiment of the device comprises at least three conjoined pieces instead of one, vascular surgeons have greater flexibility when it is determined during implantation and repair surgery that the overall length and/or arrangement of the shunt device needs to be shortened, extended and/or modified in order to accommodate the specific physical characteristics or conditions of the implantation site. With this embodiment, for example, the vascular surgeon can easily cut one or both of the flexible shunts at the ends abutting the medial flow control unit during surgery in order to produce a shunt device having a shorter overall length. The surgeon may also decide during surgery, depending on the circumstances and desired arrangement of the shunt device under the patient's skin, to use two flexible shunts having lengths that are substantially different from each other. In addition, when one of the components in the modular arteriovenous shunt device of the present invention fails, begins to deteriorate or simply needs replacing due age or the availability of technical improvements, that component may easily be removed and replaced by the vascular surgeon without removing and replacing the entire shunt device.

Modular embodiments of the invention include an arterial anastomotic valve, a venous anastomotic valve, one or more flow sensors attached to one or both of the anastomotic valves, a medial flow control unit, two flexible shunts and a valve control system. The arterial anastomotic valve is surgically connected to an artery in the patient's arm or leg and is configured to permit blood flowing through that artery to pass into the shunt device when the valve is in the open position. The venous anastomotic valve is surgically connected to a nearby vein in the patient's arm or leg, and is configured to permit blood flowing through the shunt device to pass into the patient's vein when the valve is in the open position. The first flexible shunt, which is connected at one end to the arterial anastomotic valve and connected at its other end to the medial flow control unit, carries blood from the arterial anastomotic valve to the medial flow control unit. The second flexible shunt, which is connected at one end to the medial flow control unit and connected at its other end to the venous anastomotic valve, carries blood from the medial flow control unit to the venous anastomotic valve. During a dialysis session, both the arterial anastomotic valve and the venous anastomotic valves or opened to permit blood to flow through the two flexible shunts and the medial flow control unit, and two hypodermic needles, which are fluidly connected to the dialysis machine, are inserted into the two flexible shunts in order to carry blood from the arterial end of the shunt device into the dialysis machine for cleansing and to carry the cleansed blood from the dialysis machine back to the venous end of the shunt device.

In an alternative embodiment of the invention, there is provided a hemodialytic angioaccess device that may, or may not, incorporate the three or more conjoined pieces of the modular design. In other words, the three or more conjoined pieces is an option, but not a requirement. This embodiment comprises an AV shunt, an arterial anastomotic valve, a venous anastomotic valve, a valve control system and an integrated surveillance system that measures flow conditions in the vein, the artery, or both the vein and artery. The AV shunt may comprise two or more flexible tubes with a medial flow control unit interposed between them, so that the blood flows through the arterial anastomotic valve, through at least one flexible tube, through the medial flow control unit, through at least one other flexible tube, and then through the venous anastomotic valve. In this embodiment, however, the AV shunt may also comprise a single flexible tube extending from one anastomotic valve to the other anastomotic valve. The medial flow control unit may be attached to the single flexible tube comprising the AV shunt, so that blood flows through the medial flow control unit as it passes through the single flexible tube, or alternatively, may be directly attached only to the anastomotic valves via electrical leads and/or hydraulic fluid tubes, so that blood flowing through the single flexible tube during a dialysis treatment does not pass through the medial flow control unit.

In some embodiments, the arterial anastomotic valve may comprise a static ring, a rotating ring, and an arterial aperture formed by a cylindrically-shaped sleeve fixedly attached at one end to the first static ring and fixedly connected at its other end to the rotating ring. The venous anastomotic valve comprises a second static ring, a second rotating ring, and a venous aperture formed by a second cylindrically-shaped sleeve fixedly attached at one end to the second static ring and fixed connected at its other end to the second rotating ring. When the valve control system is activated to open the valves, the first and second rotating rings in the valves rotate in one direction (although not necessarily in the same direction), which causes the first and second cylindrical sleeves to untwist, thereby expanding the diameter of the arterial and venous apertures and increasing the rate blood is permitted to flow through those apertures. When the valve control system is activated to close the valves, the first and second rotating rings rotate in the opposite direction, which causes the first and second cylindrical sleeves to twist together, thereby contracting the arterial and venous apertures to reduce the rate at which blood is permitted to flow through the valves. When the patient is not undergoing dialysis treatment, the arterial and venous apertures are preferably sufficiently contracted to entirely prevent blood from flowing into or through the shunt device.

In preferred embodiments, the valve control system uses flexible fluid tubes, hydraulic fluid, fluid-filled chambers, and a biasing means (such as a spiral spring, a gas spring, a compressible foam or a compressible fluid) to force the rotating rings in the anastomotic valves to rotate in a manner that causes the cylindrically-shaped sleeves to untwist and twist, thereby forming iris-like apertures that open and close to permit or prevent the flow of blood into and out of the shunt devices. Thus, as will be described in more detail below, components of the valve control system may be located inside and between some of the other components of the device, such as the arterial anastomotic valve, the venous anastomotic valve and the medial flow control unit.

In particular, the valve control system in some embodiments comprises a first spiral chamber disposed about the circumference of the arterial anastomotic valve, the first spiral chamber having an open end, a closed end and a slot running along its interior-facing side. A plunger, which is slidably enclosed in the first spiral chamber, is biased toward the open end of the first spiral chamber by a spiral or helical spring or some other suitable biasing means. A rod having one end connected to the plunger and the other end connected to a fixed position on the perimeter of the first rotating ring passes through the slot so that movement of the plunger through the spiral chamber caused by pressure exerted by the hydraulic fluid or the biasing means causes the first rotating ring to rotate in the same direction as the plunger's movement, thereby opening or closing the aperture formed by the walls of the twisting and untwisting cylindrical sleeve attached to the first rotating ring.

The open end of the first spiral chamber is in fluid communication with a first flexible fluid tube whose other end is fluidly coupled to a bibb on the medial flow control unit. This flexible fluid tube may or may not be at least partially filled with hydraulic fluid at all times, even when the valve control system is not currently in use. The bibb on the medial flow control unit is fluidly coupled to a fluid injection port attached to the medial flow control unit. When a dialysis session is about to begin, additional hydraulic fluid is injected into the fluid injection port (this may be accomplished, for example, with a hypodermic needle filled with hydraulic fluid), which causes the hydraulic fluid already inside the first flexible fluid tube, as well as some of the injected hydraulic fluid, to pass from the first flexible fluid tube into the first spiral chamber. The increased pressure exerted by the additional hydraulic fluid forces the plunger in the first spiral chamber to overcome the pressure exerted by biasing means and to move toward the closed end of first spiral chamber. As previously stated, because the plunger is fixedly connected to the perimeter of the first rotating ring, the plunger's movement through the first spiral chamber causes the first rotating ring to rotate, which untwists the walls of the twisted cylindrical sleeve, thereby expanding the arterial aperture to permit blood to flow into and through the shunt device.

When a dialysis session is finished, hydraulic fluid is extracted from the fluid injection port, which causes the hydraulic fluid previously forced into the first spiral chamber to evacuate the first spiral chamber through the first flexible fluid tube, and permits the biasing means to force the plunger back toward the open end of the first spiral chamber. As the plunger moves back toward the open end of the spiral chamber, it pulls on the perimeter of the first rotating ring, which causes the first rotating ring to rotate in the opposite direction to contract the arterial aperture and gradually reduce and eventually prevent the flow of blood into the shunt device.

The components of the valve control system which are located in or connected to the arterial anastomotic valve, as described above, are substantially duplicated at the venous end of the shunt device so that the opening and closing of the iris-like aperture in the venous anastomotic valve (in order to permit or prevent blood to flow out of the device and into the patient's vascular system) may be accomplished and controlled in substantially the same manner. Thus, the valve control system further comprises a second spiral chamber disposed about the circumference of the venous anastomotic valve, which second spiral chamber has a second open end, a second closed end and a second slot running along its interior-facing side. A second plunger, which is slidably enclosed in the second spiral chamber, is biased toward the second open end by a second biasing means (such as a second spiral spring). There is also a second rod extending through the second slot, the second rod having one end connected to the second plunger and the other end connected to a fixed position on the perimeter of the second rotating ring, so that when the second plunger moves back and forth through the second spiral chamber, the movement causes the second rotating ring to rotate, thereby untwisting the walls of the second cylindrically-shaped sleeve to open and close the venous aperture to permit or prevent the flow of blood through that aperture. A second flexible fluid tube is provided, which is also in fluid communication with both the fluid injection port attached to the medial flow control unit and the second open end of the second spiral chamber.

The second flexible fluid tube may also be at least partially filled with hydraulic fluid. Therefore, when the dialysis session is about to begin and the additional hydraulic fluid is injected into the fluid injection port attached to the medial flow control unit, at least some of the additional hydraulic fluid forces the hydraulic fluid already inside said second flexible fluid tube to pass into the second spiral chamber, thereby forcing the second plunger to move against the second biasing means toward the closed end of the second spiral chamber. The movement of the second plunger causes the second rotating ring to rotate in one direction, thereby causing the venous aperture to expand, which permits blood to flow out of the venous anastomotic valve into the patient's vein. Conversely, when the dialysis session is completed and the additional hydraulic fluid is extracted from the fluid injection port, this causes the hydraulic fluid previously forced into the second spiral chamber to evacuate the second spiral chamber, which permits the second biasing means to force the second plunger back toward the open end of the second spiral chamber, thereby causing the second rotating ring to rotate in the opposite direction to contract the venous aperture and reduce or prevent blood from flowing out of the shunt device into the patient's vein.

In an alternative arrangement, the anastomotic valves may comprise shuttle valves at the anastomosis joints, instead of iris valves, the shuttle valves having stoppers that shuttle back and forth inside valve housings in response to activation of the valve control system so as to alternatively open and close passageways through the valve housings to alternatively allow and prevent blood from flowing into and through the AV shunt, depending on the position of the stoppers.

The medial flow control unit is operable with the valve control system to independently control both the rate at which blood is permitted to enter the shunt device via the arterial anastomotic valve, and the rate at which blood is permitted to exit the shunt device via the venous anastomotic valve.

Embodiments of the present invention may also include one or more venous flow sensors attached to the venous anastomotic valve, which are configured to record data describing the flow of blood in the vicinity of the venous anastomotic valve and to transmit the data to the medial flow control unit via an electrical lead that electrically couples the venous flow sensors to the medial flow control unit. In some embodiments, the electrical lead is embedded in the flexible fluid tube carrying the hydraulic fluid used to open and close the venous valve. The purpose of the venous flow sensors is to take and record quantitative measurements of the blood flow in and around the area where the venous anastomotic valve joins with the vein, and thereby help to detect conditions, such as increased or extraordinary turbulence, which can lead to thrombosis and aneurysms. The venous flow sensors may comprise any sensors suitable for measuring the flow of fluid, including, for example, a hot-wire anemometer configured to measure the forced convective heat transfer from a thermal element to the blood, a pressure sensor or a volumetric sensor. Some embodiments of the invention may also include all three types of flow sensors, so as to permit, for instance, calculation of compliance and resistance in the blood vessels based on the speed, pressure and volume of blood passing through the blood vessels.

The medial flow control unit typically comprises a microprocessor, a memory storage device, a transceiver and a battery. As the data is recorded by the venous flow sensor and transmitted to the medial flow control unit via the electrical lead, the microprocessor is preprogrammed to cause the received data to be stored in the memory storage device. The transceiver, which is coupled to the microprocessor, is configured to receive a predetermined radio frequency signal generated by an external transmitter and pass that signal to the microprocessor. When the microprocessor receives the predetermined radio frequency signal, it is preprogrammed to retrieve the data stored in the memory storage device and cause the transceiver to wirelessly transmit the retrieved data to an external receiver using, for example, another predetermined radio frequency signal. The battery provides a power source for the microprocessor, transceiver and memory storage device.

Embodiments of the present invention may also include one or more arterial flow sensors, attached to the arterial anastomotic valve, which are configured to record data describing the flow of blood through the artery in the vicinity where the artery joins with the arterial anastomotic valve and transmit that data to the medial flow control unit for storage in the memory storage device. The data are transmitted to the medial flow control unit via a second electrical lead embedded in the flexible fluid tube interposed between the arterial anastomotic valve and the medial flow control unit. These data may be helpful in detecting arterial steal syndrome. Notably, the venous and arterial flow sensors and the microprocessor are configured to record and store blood flow data regardless of whether the patient is currently undergoing dialysis treatment. Therefore, the blood flow data collection and storage functions continue to be carried out even when the patient is away from medical technicians and medical facilities.

Turning now to the drawings, FIG. 1 shows an exemplary embodiment of a modular arteriovenous shunt device according to the present invention, when it is subcutaneously implanted in a patient's left forearm 10. As shown in FIG. 1, the modular arteriovenous shunt device includes an arterial anastomotic valve 12, a venous anastomotic valve 14, a medial flow control unit 16, a first flexible shunt 18, and a second flexible shunt 20. The arterial anastomotic valve 12 is surgically attached to the wall of the patient's artery 22 in such a way that when arterial anastomotic valve 12 is in the open position, at least some portion of the blood flowing through the artery 22 is permitted to pass into and through arterial anastomotic valve 12 and first flexible shunt 18. First flexible shunt 18 carries the blood from arterial anastomotic valve 12 to medial flow control unit 16. The venous anastomotic valve 14 is surgically attached to vein 24 in such a way that, when the venous anastomotic valve 14 is in the open position, blood flowing from the medial flow control unit 16 is permitted to pass into and through second flexible shunt 20, where it then passes into and through venous anastomotic valve 14, and then emptied into the patient's vein 24.

A hypodermic needle (not shown in FIG. 1) fluidly coupled to an external dialysis machine (also not shown in FIG. 1) may be inserted into first flexible shunt 18 anywhere along its length in order to channel some of the blood flowing through first flexible shunt 18 out of the shunt device and into the dialysis machine for cleansing. Any blood flowing through first flexible shunt 18 that does not exit the shunt device via the hypodermic needle inserted into first flexible shunt 18 continues to flow toward and through the medial flow control unit 16, through the second flexible shunt 20, through the venous anastomotic valve 14 and finally into the patient's vein 24. A second hypodermic needle (not shown in FIG. 1) fluidly coupled to the dialysis machine is inserted into the second flexible shunt 20 anywhere along its length. The second hypodermic needle carries cleansed blood from the dialysis machine to the second flexible shunt 20, whereupon the cleansed blood is mixed with any blood that has flowed through medial flow control unit 16 and then returned to the patient's body via venous anastomotic valve 14 and patient vein 24.

As shown in FIG. 1, the modular arteriovenous shunt device also includes a first flexible fluid tube 26 that fluidly couples medial flow control unit 16 to arterial anastomotic valve 12. A second flexible fluid tube 28 fluidly couples medial flow control unit 16 to venous anastomotic valve 14. As will be discussed in more detail below, first flexible fluid tube 26 and second flexible fluid tube 28 are also fluidly coupled to a fluid injection port 30 attached to medial flow control unit 16, which provides a mechanism for introducing hydraulic fluid into the device and extracting hydraulic fluid from the device in order to control the opening and closing of the apertures in arterial anastomotic valve 12 and venous anastomotic valve 14.

First flexible shunt 18, second flexible shunt 20, first flexible fluid tube 26 and second flexible fluid tube 28 are typically manufactured from polytetrafluoroethylene (PTFE). However, any other biocompatible material may be used without departing from the scope of the claimed invention. Preferably, but not necessarily, the flexible shunts have a diameter that is roughly equivalent to the diameter of the arterial and venous anastomotic valves. The flexible fluid tubes may have diameters somewhat larger or smaller than the diameters of the flexible shunts, depending, for example, on the volume of hydraulic fluid and the pressure required to smoothly operate the anastomotic valves.

Figure 2:
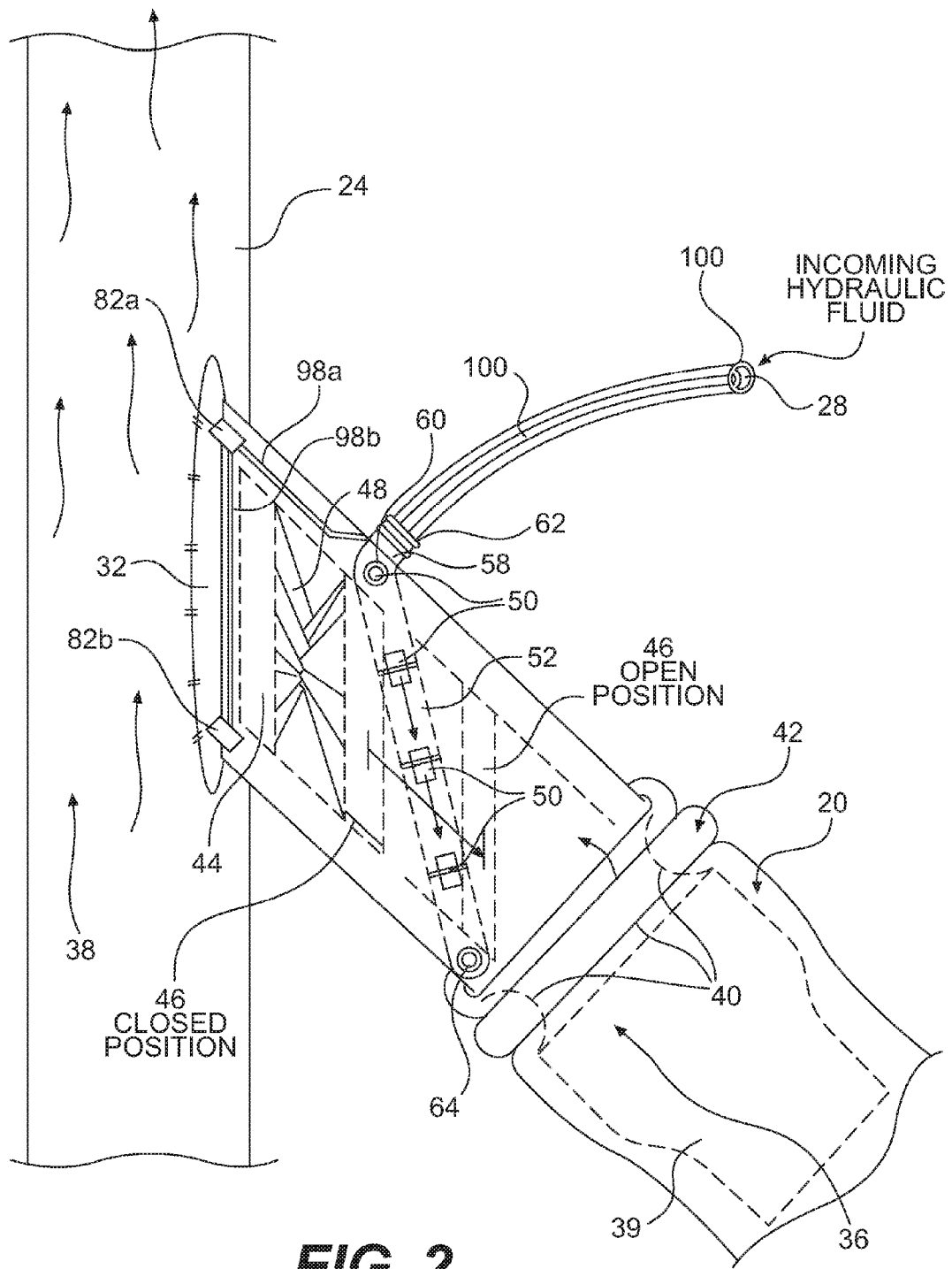
FIG. 2 provides a more detailed view of a venous anastomotic valve according to one embodiment of the invention.

FIG. 2 provides a more detailed view of venous anastomotic valve 14 according to one embodiment of the invention. As shown in FIG. 2, one end of venous anastomotic valve 14 includes a flange 32, which is sutured to the vein 24 (or artery in the case of an arterial anastomotic valve) when the device is implanted in a patient. The flanged end of the venous anastomotic valve 14 is also beveled in order to facilitate attaching the venous anastomotic valve 14 to the vein 24 at an angle of less than ninety degrees, which reduces the amount of turbulence that might otherwise occur as blood 36 flowing through the device and venous anastomotic valve 14 collides with blood 38 already moving through vein 24.

The other end of venous anastomotic valve 14 (i.e., the end connected to second flexible shunt 20) is somewhat tapered so that it will fit easily, but snugly, into the open end of second flexible shunt 20. The tapered end 39 of the venous anastomotic valve 14 also contains an annular-shaped notch 40, which provides a stable and secure resting position for a clamp or rubber band 42 that may be used to fasten second flexible shunt 20 onto the tapered end 39 of venous anastomotic valve 14 during the implantation procedure and hold second flexible shunt 20 in place thereafter. The tapered end 39 of venous anastomotic valve 14 may alternatively contain ridges and/or protrusions (not shown in FIG. 2) on or about its outer surface to provide a stable and secure resting coupling between venous anastomotic valve 14 and second flexible shunt 20. As shown in FIG. 2, for example, the second flexible shunt 20 is fastened to the venous anastomotic valve 14 by pushing the second flexible shunt 20 past an annular notch 40 carved into the tapered end 39 of the venous anastomotic valve 14 and then seating rubber band 42 on top of the second flexible shunt 20 so that the rubber band 42 is firmly seated in the notch 40 and the second flexible shunt 20 is firmly compressed by the rubber band 42 against the outer walls of the tapered end 39. Thus, fastening the flexible shunts to the anastomotic valves is relatively straight forward, does not require special tools or surgical instruments, and can easily be accomplished by the vascular surgeon during the implantation procedure, even if it becomes necessary to cut away a portion of the flexible shunt before it is attached.

Inside venous anastomotic valve 14 there is an iris valve-like structure comprising a static ring 44, a rotating ring 46 and an aperture formed by the twisting walls of a cylindrically-shaped sleeve 48 having one end that is fixedly attached to the static ring 44 and an opposite end that is fixedly attached to the rotating ring 46. The static ring 44 is preferably located as close as possible to the beveled and flanged end of the venous anastomotic valve 14, while the rotating ring 46 is located closer to (but not necessarily adjacent to) the tapered end 39. When the shunt device is first implanted and dialysis is not occurring, the rotating ring 46 is positioned so that the wall of the sleeve 48 is twisted, causing the segments of the wall to fold over each other in a helical arrangement. This position causes the aperture formed by the walls of the sleeve 48 to contract and form a barrier through which blood 36 cannot flow. The position for the rotating ring 46 while the aperture is closed in this manner is indicated in FIG. 2 with the label "46 (Closed Position)."

When a hemodialysis session is about to begin, the rotating ring 46 is rotated approximately 180 degrees from its closed position so that wall segments of the sleeve 48 untwist and unfold, thereby expanding the aperture formed by the walls of sleeve 48 into a cylindrically-shaped open passageway through which the blood 36 is permitted to flow. As the rotating ring 46 rotates to untwist the sleeve 48 and open the passageway, it also changes its vertical and horizontal position within the venous anastomotic valve 14, moving further away from the static ring 44 (i.e., down and to the right in FIG. 2) and coming to rest in the position indicated in FIG. 2 with the label "46 (Open Position)."

When both the arterial anastomotic valve 12 and the venous anastomotic valve 14 are open, the device permits blood to flow out of the artery 22, into and through the arterial anastomotic valve 12, through the first flexible shunt 18, through the medial flow control unit 16, through the second flexible shunt 20, through the venous anastomotic valve 14 and finally into the vein 24. While this is occurring, hypodermic needles may be inserted into one or both of the flexible shunts in order to extract blood from and return blood to the patient's vascular system.

After the hemodialysis session is completed, the rotating ring 46 is rotated about 180 degrees in the opposite direction, which causes the walls of the sleeve 48 to twist and fold over each other again, thereby contracting the diameter of the aperture to cut off the flow of blood 36. Closing the aperture also causes the rotating ring 46 to travel toward the static ring 44 again (i.e., up and to the left in FIG. 2) and come to rest in its initial position. The vertical and horizontal travel of the rotating ring as it opens and closes may be guided and supported by notches and/or grooves (not shown in FIG. 2) along the interior wall surfaces of the venous anastomotic valve 14.

Valve Control System

In the embodiment of the invention shown in FIGS. 1 and 2, the opening and closing of the venous anastomotic valve 14 and arterial anastomotic valve 12 (and, more particularly, the rotation of the rotating rings in those valves) is powered by a valve control system. The components of the valve control system include a plunger 50 attached to the perimeter of rotating ring 46. The plunger 50 is pushed by hydraulic fluid through a 180 degree arc toward the far end of a spiral (or helically-shaped) chamber disposed about the circumference of the cylindrically-shaped body of venous anastomotic valve 14. The plunger 50 is connected to a rod 54 (best shown in FIGS. 4A-4C and 5A-5B), which extends through a slot 56 (best shown in FIG. 6) on the interior-facing side of the spiral chamber 52 and attached to a fix point on the perimeter of the rotating ring 46. Thus, when the plunger 50 moves, so does the rotating ring 46. It should be noted that, in the embodiment of the invention shown in FIG. 2, there is only one plunger 50 in the spiral chamber 52 (although multiple plungers may also be used without departing from the scope of the invention). Thus, the illustration in FIG. 2 should not be construed to show five different plungers. Rather, FIG. 2 is meant to show the single plunger 50 as it passes though five different locations in spiral chamber 52.

Hydraulic fluid is introduced into the spiral chamber 52 via second flexible tube 28 interposed between venous anastomotic valve 14 and the medial flow control unit 16. The second flexible fluid tube 28 may be physically attached to a bibb 58 on the perimeter of venous anastomotic valve 14, the bibb being in fluid communication with the open end 60 of the spiral chamber 52. The second flexible fluid tube 28 is secured to the bibb 58 by compressing the end of the second flexible tube 28 between the outside of the bibb 58 and a clamp or rubber band, similar to the method used to fasten and hold second flexible shunt 20 to the tapered end 39 of the venous anastomotic valve 14.

Figure 3A:
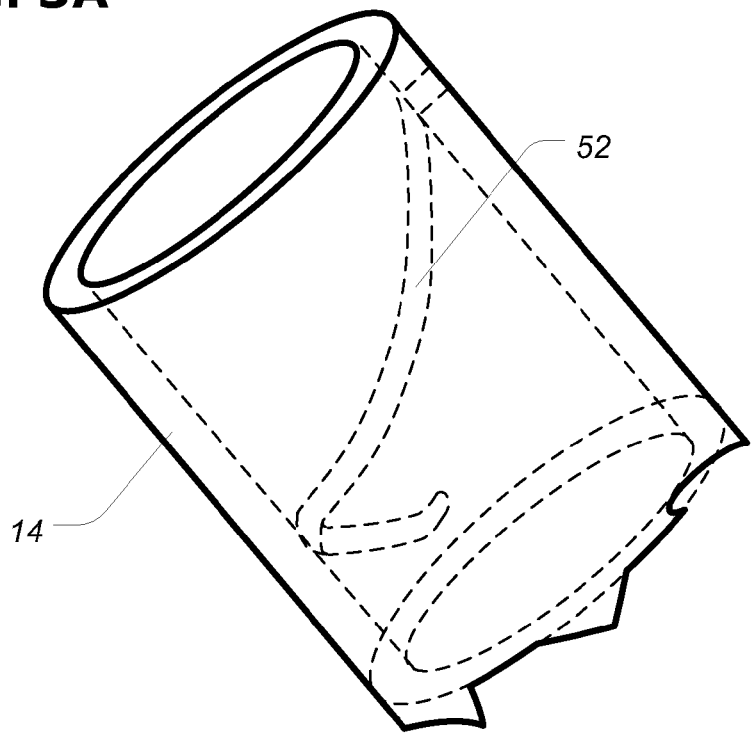
FIGS. 3A and 3B illustrate two examples of the configuration of the housing and spiral chambers in the anastomotic valves according to embodiments of the invention.
Figure 3B:
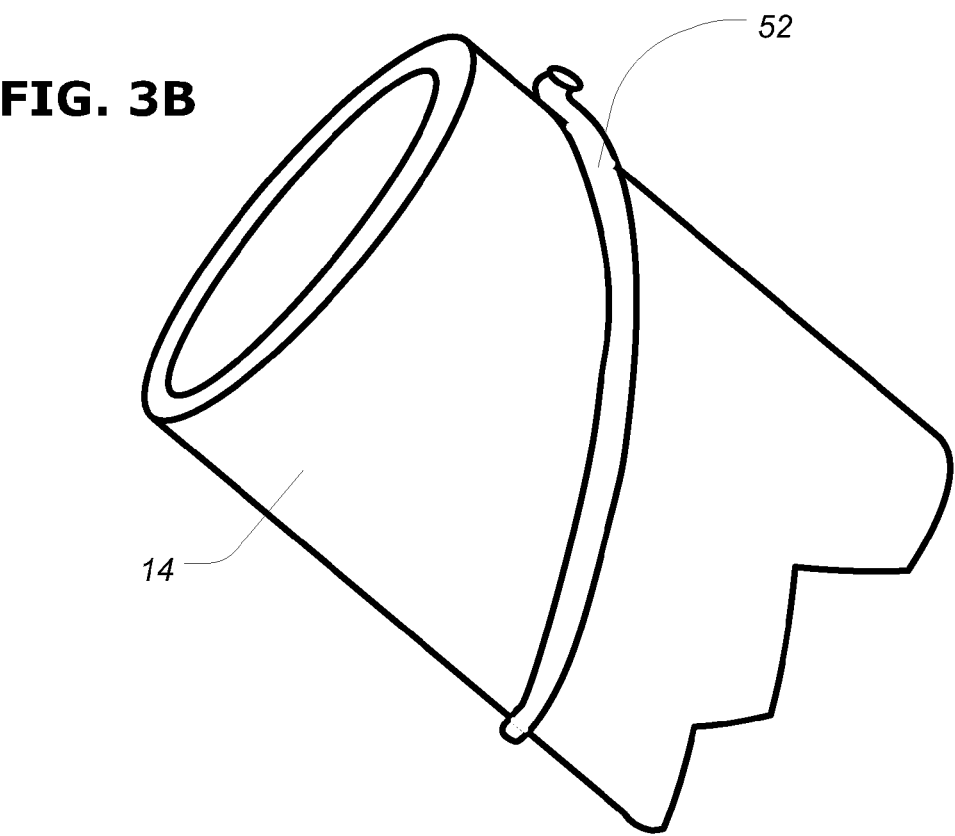

The spiral chamber 52 may be located completely inside the venous anastomotic valve 14 (as best shown in FIGS. 2 and 3A). However, it may also be located wholly or partially outside the exterior wall of venous anastomotic valve 14 (as best shown in FIG. 3B). The end of the spiral chamber 52 opposite from the open end 60 is closed. However, between the closed end 64 and the plunger 50, there is provided a means for biasing the plunger toward the open end 60. The biasing means, which may comprise, for example, a helical metal spring, a gas spring, a compressible foam material, a compressible fluid, or some combination of two or more of these biasing structures, keeps venous anastomotic valve closed when no dialysis session is in progress. In the exemplary embodiment shown in the figures, the biasing means comprises a spiral spring 66 (See FIGS. 4A-4C).

FIGS. 4A, 4B, and 4C show, respectively, cross-sectional views of the venous anastomotic valve 14 in the closed, half open and fully-open positions. In this case, the biasing means comprises a spiral (or helical) spring 66 placed at the closed end 64 of the spiral chamber 52. As shown by these figures, when a sufficient quantity of hydraulic fluid is pushed into the spiral chamber 52 through its open end 60, the plunger 50 is forced to move (in a counterclockwise direction) about 180 degrees around the circumference of the venous anastomotic valve 14, the movement of the plunger being dictated by the spiral chamber 52 in which it is enclosed. This movement causes the rotating ring 46 to rotate 180 degrees counterclockwise; thereby opening the aperture 68 formed by the walls of the cylindrically-shaped sleeve 48, and compressing the spiral spring 66 in the closed end 64 of the spiral chamber 52. (See FIGS. 4B and 4C). While the spiral chamber 52 remains full of hydraulic fluid, the anastomotic valves remain open, which permits blood to flow through the arterial and venous anastomotic valves 12 and 14, the first and second flexible shunts 18 and 20, and the medial flow control unit 16, which provides medical technicians with access to the flow of blood in the shunts 18 and 20 for dialysis. When the dialysis is completed, the hydraulic fluid is evacuated from the spiral chamber 52 and the spiral spring 66 compressed against the closed end 64 of the spiral chamber 52 begins to decompress and exert sufficient force on the plunger 50 to move the plunger 50 back around the circumference of the venous anastomotic valve 14 in a clock-wise direction, thereby causing the rotating ring 46 to rotate in a clock-wise direction toward its original position. This rotation causes the aperture 68 formed by the walls of the sleeve 48 to contract and close, which cuts off the blood flow. (See FIG. 4A).

Figure 5A:
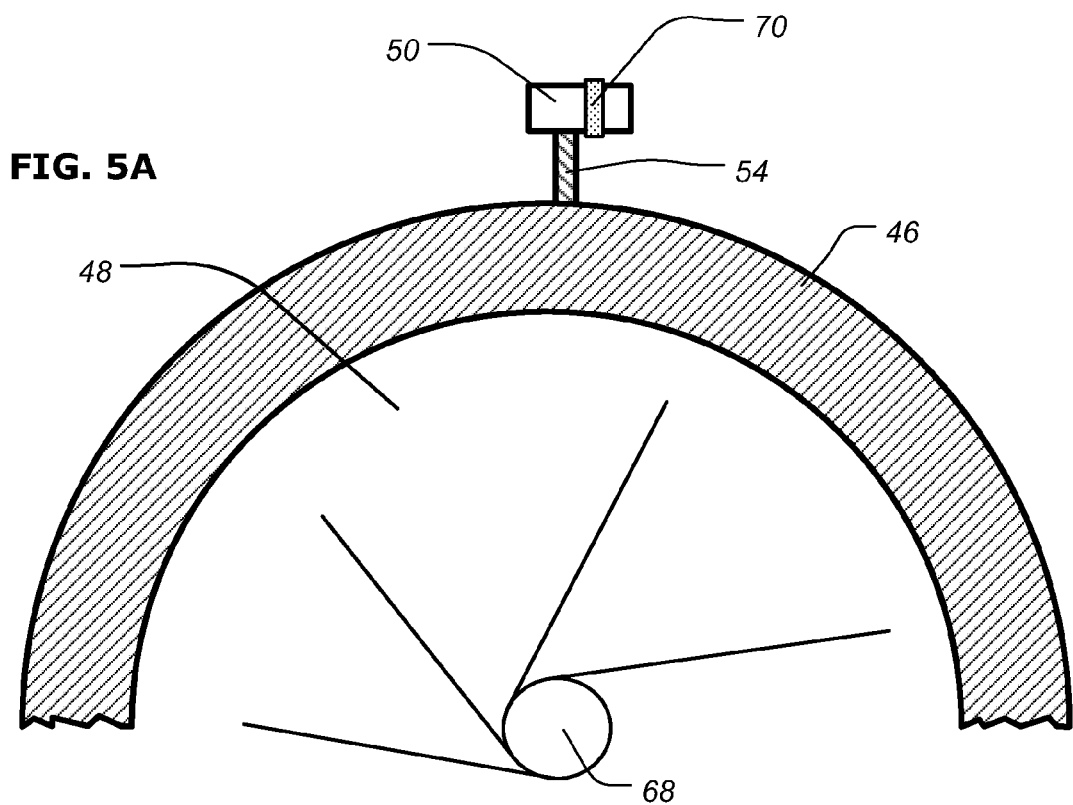
FIGS. 5A, 5B and 6 contain cross-sectional diagrams illustrating the arrangement of the rotating ring, sleeve, rod, slot and plunger in an exemplary embodiment of the invention.
Figure 5B:
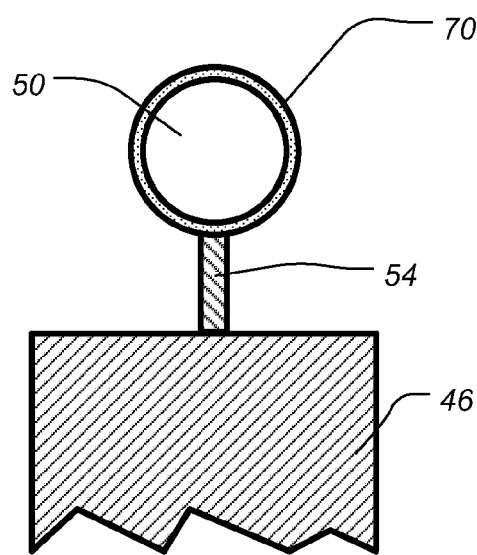
Figure 6:
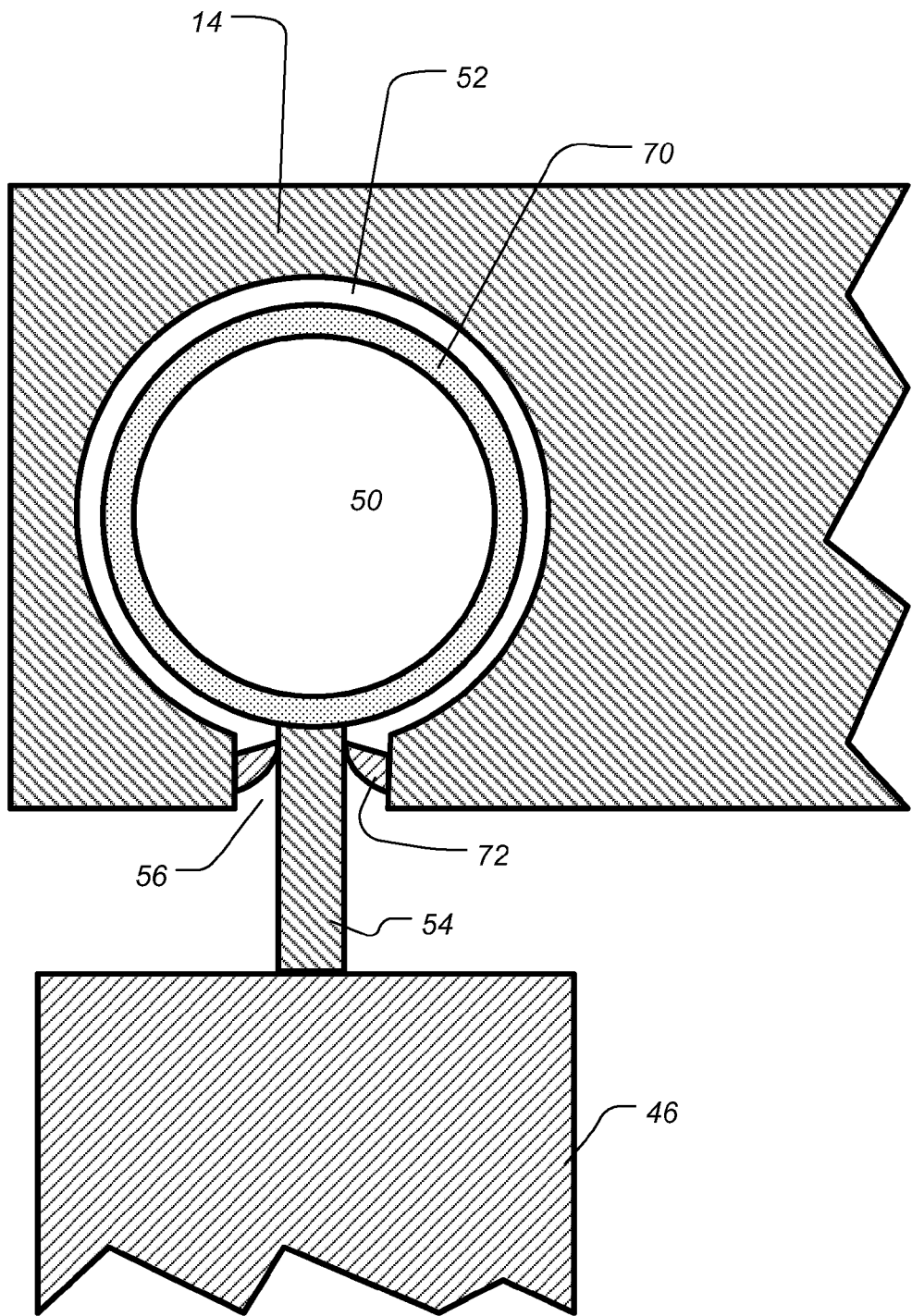

FIGS. 5A, 5B and 6 contain cross-sectional diagrams illustrating the arrangement of the rotating ring 46, sleeve 48, rod 54, slot 56 and plunger. As shown in these figures, the plunger 50 may be fitted with a gasket 70 in order to reduce and/or limit the volume of hydraulic fluid that can squeeze between the plunger 50 and the interior walls of spiral chamber 52 to escape the spiral chamber 52 through the open end 60. Slot 56 may also be fitted with gaskets, flanges and/or bristles 72 in order to prevent hydraulic fluid from escaping the spiral chamber 52 by squeezing through the spaces between the rod 54 and the walls of the slot 56.

It should be noted that the configuration and operation of the arterial anastomotic valve (not shown in the figures) is substantially the same as the configuration and operation of the venous anastomotic valve, except that the blood flows are reversed.

Medial Flow Control Unit (MFCU)

Figure 7:
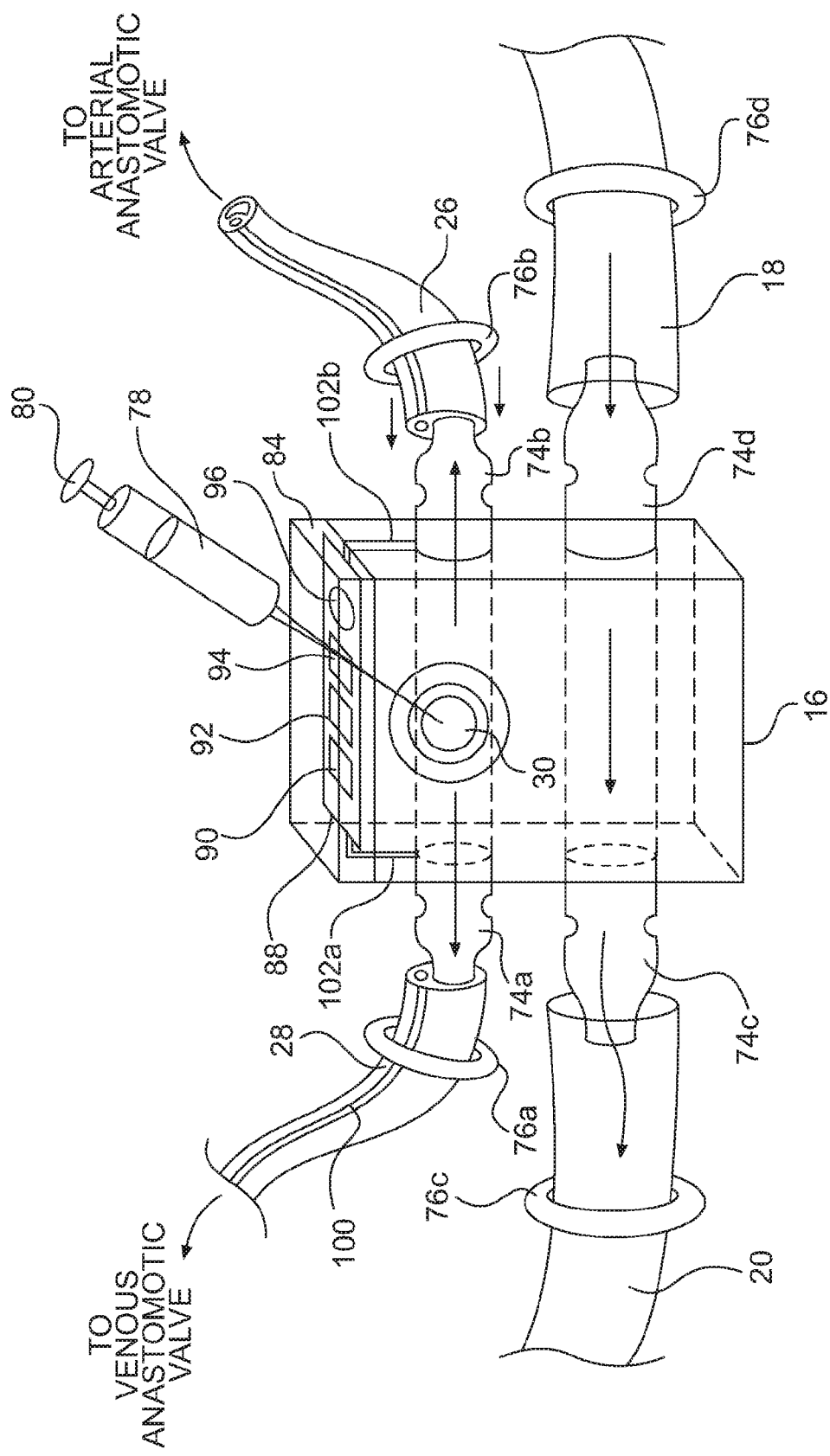
FIG. 7 shows a more detailed view of the medial flow control unit in embodiments of the invention.

FIG. 7 shows a more detailed view of the medial flow control unit 16. As shown in FIG. 7, the ends of the first and second flexible shunts 18 and 20 and the first and second flexible fluid tubes 26 and 28 are connected to bibbs 74a-74d on the medial flow control unit 16 using, for instance, rubber bands 76a-76d or some other suitable fasteners. Preferably, the bibbs 74a-74d are tapered, notched and/or grooved at their distal ends to facilitate sliding them into and securing them to the open ends of the flexible shunts 18 and 20 and flexible fluid tubes 26 and 28. The hydraulic fluid 78 used to move the rotating rings 46 in the arterial and venous anastomotic valves 12 and 14 is introduced into the flexible fluid tubes 26 and 28 via the fluid injection port 30 attached to the medial flow control unit 16. The fluid injection port 30 is in fluid communication with both of the flexible fluid tubes 26 and 28 leading to the spiral chambers 52 in the arterial and venous anastomotic valves 12 and 14.

More specifically, when a hemodialysis session is about to begin, a hypodermic needle 80 is inserted into the fluid injection port 30 on the medial flow control unit 16 to inject a predetermined volume of hydraulic fluid 78 (e.g., saline solution or any other biocompatible solution) into the medial flow control unit 16. The hydraulic fluid 78 is then forced through the bibbs 74a and 74b on the medial flow control unit 16, through the flexible fluid tubes 26 and 28 and into the open ends 60 of the spiral chambers 52 in the arterial and venous anastomotic valves 12 and 14. As previously-stated, this causes the rotating rings in the arterial and venous anastomotic valves 12 and 14 to rotate to their open positions, thereby permitting blood to flow out of the artery 22, into the arterial anastomotic valve 12, through the first flexible shunt 18, through the medial flow control unit 16, through the second flexible shunt 20, through the venous anastomotic valve 14, and finally, out into the vein 24.

Integrated Surveillance System

A major cause of failure associated with AV shunt devices is arterial steal, thrombosis of the venous anastomosis and chronic draining of the vein. To reduce and mitigate these problems, embodiments of the present invention include an integrated surveillance system configured to provide quantitative measurements of blood flow through the vessels in the vicinity of the arterial and venous anastomotic valves 12 and 14. More specifically, the beveled and flanged end of venous anastomotic valve 12 is equipped with one or more flow sensors 82a and 82b (best illustrated in FIG. 2), which are electrically coupled to a processor compartment 84 in the medial flow control unit 16 that houses a printed circuit board 88 (PCB) containing one or more microprocessors 90, memory modules 92, transceivers 94 and batteries 96. These components all operate together to collect, store and wirelessly transmit blood flow data to an external receiver (not shown in FIG. 7).

While it is not the only way, one way of measuring blood flow involves using microelectromechanical systems (MEMS). MEMS fluid anemometers, for example, are capable of measuring the flow of blood based on the rate of heat loss from a heated thermal sensing element to the surrounding blood as it moves past the element. A voltage applied across the thermal sensing element causes its temperature to increase as the current increases. In the blood flow, the blood absorbs the heat from the sensor by convection, thereby lowering the temperature of the sensor element and resulting in a decreased electrical resistance. Therefore, the voltage drop across the powered resistor can be used to define a parameter which correlates to the flow of blood.

Returning to the venous anastomotic valve diagram of FIG. 2, it can be seen that two MEMS thermal sensing elements 82a and 82b are coupled to the beveled edge of the venous anastomotic valve 14 so that they extend part-way into the path of the blood 38 flowing through the vein 24. FIG. 2 also shows how electrical wire leads 98a and 98b, embedded in the body of the venous anastomotic valve 14, provide electrical connectivity between the MEMS thermal sensing elements 82a and 82b and the bibb 58 (preferably manufactured from a MRI-compatible metal, such as titanium) to which the flexible fluid tube 28 is attached. Each flexible fluid tube 26 and 28 has embedded within it, one or more insulated electrical leads 100 that provide electrical connectivity between the bibb 58 on the venous anastomotic valve 14 and the bibb 74a on the medial flow control unit 16. As shown in FIG. 7, the medial flow control unit 16 is equipped with another set of electrical leads 102a and 102b, which electrically couple bibbs 74a and 74b with the printed circuit board 88 located within the processor compartment 84. The electrical leads 98a, 98b, 102a and 102b are used to transmit low voltage data signals from the MEMs thermal sensors 82a and 82b in the arterial and venous anastomotic valves 12 and 14 to the microprocessor 90, which stores the data in the one or more memory modules 92 using known digital or analog data storage techniques.

Although not shown in the figures, the arterial anastomotic valve 12 may also be equipped with MEMS thermal sensing elements and electrical leads, so that blood flow measurements may also be collected from the areas in the artery adjacent to the arterial anastomotic valve and stored by the microprocessor in the one or more memory modules 90 on the printed circuit board 88.

A transceiver 94 on the printed circuit board is linked to the microprocessor 90. When the transceiver 94 receives a predetermined radio frequency signal from an external transmitter (not shown in FIG. 7), the microprocessor is configured (using well-known microprocessor programming techniques) to retrieve the blood flow data from the one or more memory modules 92 and then cause the transceiver 94 to wirelessly transmit the retrieved blood flow data to an external receiver. See, for example, U.S. Pat. No. 6,434,429, the disclosure of which is incorporated herein by reference, for a more detailed discussion of known close- and long-range telemetry techniques for implantable devices.

FIG. 8 shows an exemplary embodiment of a shuttle valve 200 for hemodialytic angioaccess according to an embodiment of the invention. As shown in FIG. 8, shuttle valve 200 comprises a valve housing 202, having a skirt 204 for surgically attaching the valve housing 202 over an incision or other opening (not shown in FIG. 8) that the surgeon makes in a blood vessel 206, such as a vein or artery, prior to suturing the skirt 204 to blood vessel 206 so that the entire opening or incision is completely surrounded by the skirt 24 and no fluid can pass out of the blood vessel 206 without passing through the valve housing 202. The valve housing 202 has an orifice 208 on the side of the valve housing 202 facing the incision in the blood vessel 206. A shunt connector 210 is connected to the valve housing 202 on the side of valve housing 202 opposite the blood vessel 206. Preferably, the shunt connector 210 includes an annular-shaped notch 212 (best shown in FIGS. 12 and 13), which provides a stable and secure resting position for a clamp or rubber band 214 that may be used to fasten an AV shunt 216 over the end 218 of shunt connector 210 during the implantation procedure and hold AV shunt 216 firmly in place thereafter. The end 218 of shunt connector 210 may alternatively contain ridges and/or protrusions (not shown in the figures) on or about the distal end of its outer surface to provide a stable and secure resting place for a clamp or rubber band 214 used for coupling the AV shunt 216 to the shunt connector 210.

Valve housing 202 also has an electrical connector 220 adapted to accept and engage with an electrical lead (not shown in FIG. 8), which electrically couples the electrical connector 220 with a printed circuit board, microprocessor and/or memory storage device located, for example, in a processor compartment of a medial flow control unit, such as the processor compartment 84 and the medial flow control unit 16 shown in FIG. 7 and described above. Accordingly, low voltage data signals may be carried from the electrical connector 220 to the microprocessor via the electrical lead. To facilitate connecting the electrical lead to the electrical connector 220, the electrical connector 220 may have a threaded tip 222 so that an electrical lead having a corresponding threaded tip may be easily screwed onto the threaded tip 222 by the vascular surgeon during the implantation procedure. It is understood, however, that a variety of other types of tips may be used on the electrical connector 220, as necessary or desirable, to provide a stable electrical connection for carrying data signals produced by sensors located in the shuttle valve 200 to data processing components, such as the microprocessor, which are located away from the shuttle valve 200.

Figure 12:
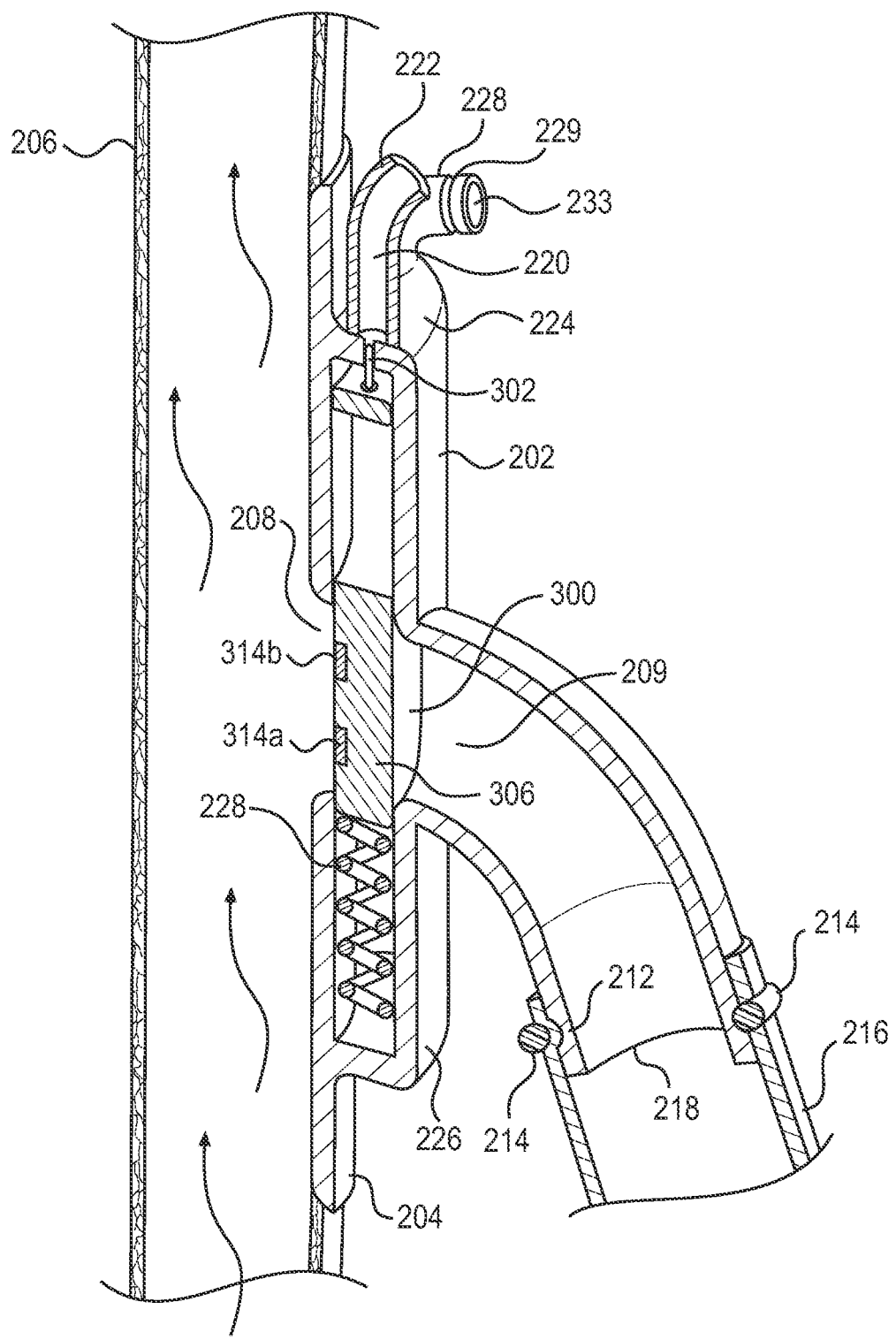
FIGS. 12 and 13 show, respectively, cross-sectional views of the shuttle valve depicted in FIG. 8, when the stopper is located in the closed position (FIG. 12) and in the open position (FIG. 13).
Figure 13:
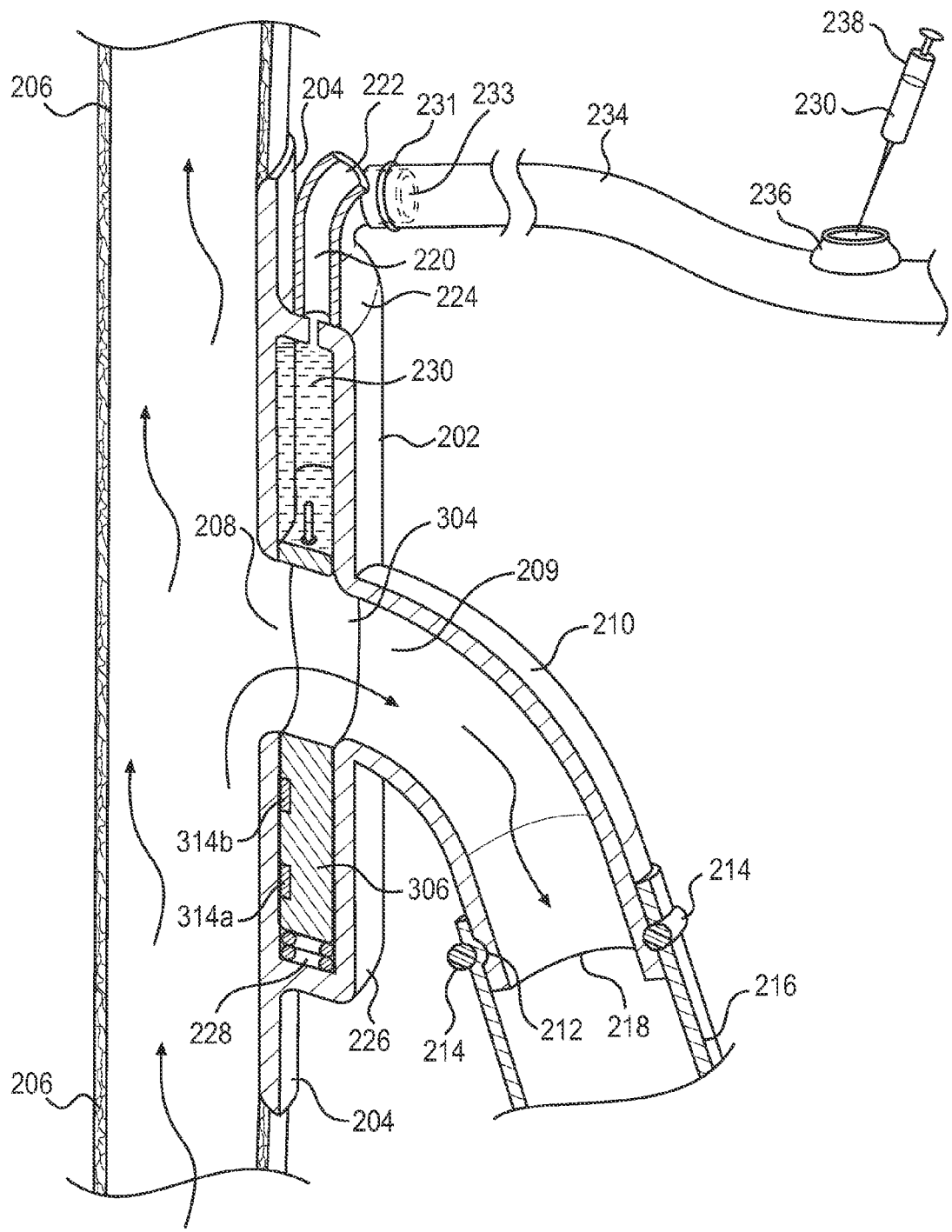

As indicated by the phantom lines of FIG. 8, shuttle valve 200 further includes a stopper 300 that is movably disposed on the interior the valve housing 202. As shown best in FIG. 9, the stopper 300 is shaped so that it substantially conforms in width, depth and curvature to the width, depth and curvature of the interior of the valve housing 202. As shown in FIGS. 8, 12, and 13, however, the length of stopper 300 is substantially shorter than the length of the interior of valve housing 202 so as to permit the stopper 300 to easily slide back and forth between the top end 224 and the bottom end 226 of the valve housing 202 in response to mechanical forces applied at one or both of those ends of the valve housing 202.

Accordingly, a valve control system is provided to supply the mechanical forces necessary to move stopper 300 back and forth between the top end 224 and the bottom end 226 of the valve housing 202. In particular, in the bottom end 226 of valve housing 202, there is a spring 228 (best shown in FIG. 12), which biases the stopper 300 toward the top end 224 of valve housing 202, so that when the spring 228 is in an uncompressed state, as shown in FIG. 12, the stopper 300 is forced against the top end 224 of valve housing 202. Typically, the spring 228 will remain in the uncompressed state and the stopper 300 will remain at the top end 224 of the valve housing 202, as shown in FIG. 12, whenever the patient is not currently undergoing dialysis treatment. At the top end 224 of the valve housing 202, there is a hydraulic connector 228 configured to admit to the interior chamber of the valve housing 202 a sufficient volume of biocompatible fluid 230 to overcome the opposing force supplied by the spring 228 and force the stopper 300 in a downward direction toward the bottom end 226 of valve housing 202, thereby compressing the spring 228, as illustrated in FIG. 13.

Although the stopper 300 is shown in the figures as comprising a substantially linear plate, slidably disposed within the valve housing, it will be understood that the stopper may be formed into other shapes without departing from the scope of the claimed invention, so long as the stopper is capable of blocking and unblocking the pathway that permits blood to flow through the valve housing. In some embodiments, for example, the stopper may comprise a circular disc (not shown in the figures), rotatably disposed within the valve housing, so that upon application of suitable mechanical force, the disc rotates so that an aperture and an apron on the disc are alternatively moved into and out of position over the pathway.

As shown in both FIGS. 12 and 13, the hydraulic connector 228 also preferably has about its distal end 233 an annular notch 229, which provides a stable and secure resting position for a clamp or rubber band 231 that may be used to fasten a flexible hydraulic fluid tube 234 onto the distal end 233 of hydraulic connector 228 during the implantation procedure and hold the flexible hydraulic fluid tube 234 in place thereafter. The other end of the flexible hydraulic fluid tube 234 is fluidly coupled to a fluid injection port 236. See FIG. 13.

Before a dialysis treatment is to begin, a hypodermic needle 238 is inserted into a diaphragm on the fluid injection port 236 to inject biocompatible hydraulic fluid 230 into the flexible hydraulic fluid tube 234. The flexible hydraulic fluid tube 234 carries the hydraulic fluid 230 to the valve housing 202, whereupon it passes through the hydraulic connector 228 and into the valve housing 202, thereby causing the stopper 300 to compress the spring 228 and move to the bottom of the valve housing 202. At this point, blood will be permitted to flow through shuttle valve 200 and the AV shunt 216 so that additional hypodermic needles (not shown) can be inserted into the AV shunt 216 to draw out blood for cleansing. When the dialysis treatment is completed, the hypodermic needle 238 is again employed to draw hydraulic fluid 230 from the fluid injection port 236, thereby evacuating hydraulic fluid 230 from the valve housing 202, allowing the spring 228 to decompress and force the stopper 300 to move again toward the top end 224 of the valve housing 202. Thus, it will be noted that the stopper 300 is typically lodged at the bottom end 226 of the valve housing 202, as shown in FIG. 13, whenever the patient is undergoing dialysis treatment, and lodged at the top end 224 of the valve housing 202, as shown in FIGS. 8 and 12, at all other times.

Returning to FIG. 9, it will be observed that the stopper 300 has an aperture 304 and an apron 306. As illustrated best in FIGS. 8 and 12, the apron 306 obstructs the path between the orifice 208 and the shunt connector 210 on the valve housing 202 whenever the stopper 300 is forced against the top end 224 of the valve housing 202, thereby blocking the path and preventing the flow of fluid from the blood vessel 206 into the shunt connector 210. Since no fluid flowing through the blood vessel 206 can pass through the apron 306 and the valve housing 202 into the shunt connector 210 while the apron 306 obstructs the path to the shunt connector 210, the shuttle valve 200 is said to be in a "closed" position. The closed position is illustrated in FIG. 12.

However, when the stopper 300 is forced to the bottom end 226 of the valve housing 202 by the admission and presence of hydraulic fluid 230 in the top end 224 of the valve housing 202, the aperture 304 in the stopper 300 aligns with the orifice 208 and the mouth 209 of the shunt connector 210 so as to permit a portion of the fluid, such as blood, flowing through the blood vessel 206 to freely pass into and through the orifice 208, through the valve housing 202 and into the mouth 209 of the shunt connector 210. When the stopper 300 is in this position, and a portion of the blood flowing through the blood vessel 206 is flowing out of the blood vessel 206 and into the AV shunt 216 via the aperture 304 and the shunt connector 210, the shuttle valve 200 is said to be in the "open" position. The open position is illustrated in FIG. 13.

Figure 10:
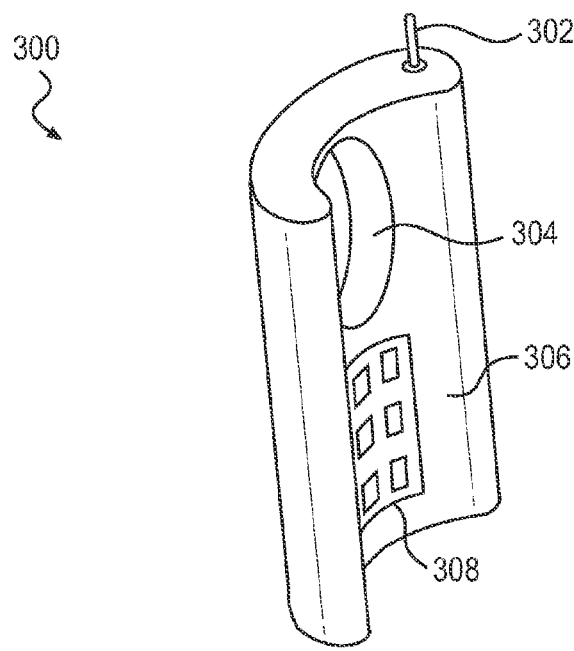
FIGS. 10 and 11 show, respectively, perspective and orthogonal views of the underside of the exemplary stopper for the shuttle valve, the exemplary stopper having an array of flow sensors configured to collect flow condition data in a blood vessel while the stopper is in the closed position.
Figure 11:
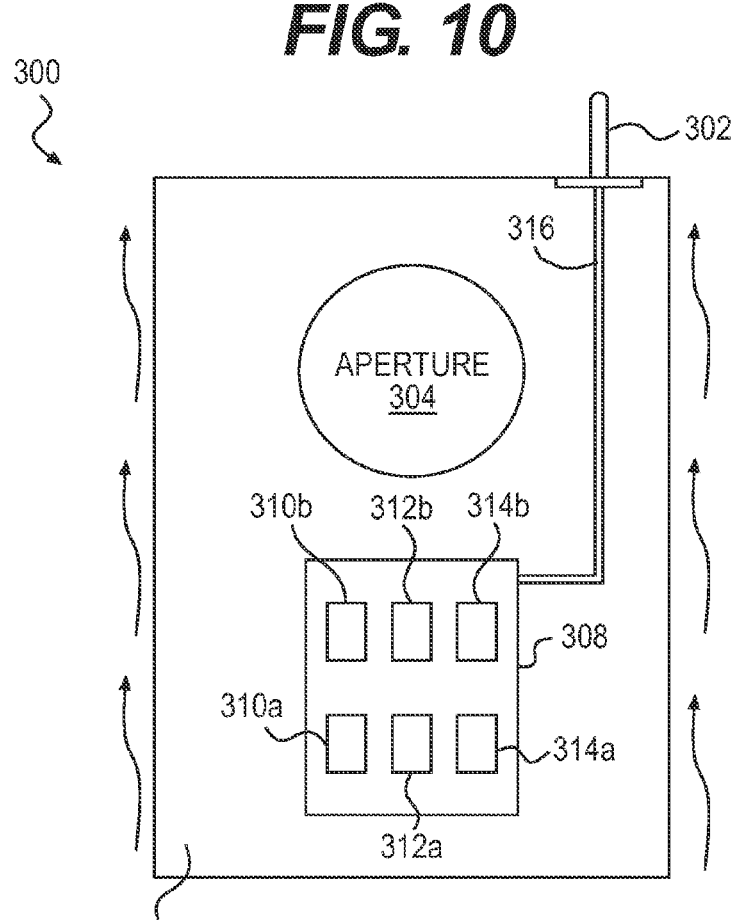

FIGS. 10 and 11 contain more detailed illustrations of the stopper 300. As shown best in FIG. 11, an array 308 of flow sensors is located on the side of the apron 306 facing the orifice 208 and the blood vessel 206. The array 308 may comprise any number and type of flow sensors configured to take quantitative measurements of various flow condition parameters of the fluid coming into contact with the sensors in the array 308. Thus, the array 308 may include a single flow sensor, a few flow sensors or a large number of flow sensors, depending on the number of flow condition parameters to be measured and the desired quality of the measurements. In preferred embodiments, however, the array 308 includes one or more MEMS hot-wire anemometers 310a and 310b, capable of measuring the flow rate of fluid based on the rate of heat loss from a heated thermal sensing element to the surrounding fluid as the blood flows over the thermal sensing elements. The array 308 may also comprise one or more pressure sensors 312a and 312b capable of measuring changes in pressure for the fluid as the fluid flows over the pressure sensing elements, or one or more volumetric sensors 314a and 314b capable of measuring changes in volume of the fluid as the fluid flows over volume sensing elements. Array 308 may also comprise one or more velocity sensors (not shown in the figures) capable of measuring the velocity of the blood as it passes over the velocity sensing elements.

When the shuttle valve 200 is in the closed position, as shown in FIG. 12, the apron 306 on the stopper 300 is positioned so that the flow sensors 310a-b, 312a-b and 314a-b on the array 308 come into contact with the circulatory system fluid passing through the blood vessel 206, and is therefore capable of taking quantitative measurements of flow conditions in the fluid while the shuttle valve 200 remains closed. It is understood, however, that the shuttle valve 200 may also be configured to operate in a manner that permits quantitative measurements to be taken while the valves are open without departing from the scope of the claimed invention.

As shown in FIGS. 10 and 11, stopper 300 also includes an electrical contact 302, mounted at one end of stopper 300, which is electrically coupled to the array 308 of sensors by an electrical lead 316, so that flow condition parameters, such as flow rate, pressure and volume, as measured by the MEMS flow sensors 310a-b, 312a-b and 314a-b in array 308, can be transmitted to the electrical contact 302 by low voltage electrical signals carried on electrical lead 316. Electrical contact 302 is in turn adapted to be received by and provide electrical connectivity with the electrical connector 220 on the valve housing 202 whenever stopper 300 is moved to the top end 224 of valve housing 202 by the expansion of the spring 228. Thus, whenever the patient is not undergoing dialysis treatment, and the shuttle valve 200 is in the closed position, low voltage electrical signals may be periodically or continuously transmitted from sensors located on the stopper 300 to the microprocessor in the medial flow control unit 16 via the electrical connection provided by electrical lead 316, the electrical contact 302, electrical connector 220 and another electrical lead (not shown) between the electrical connector 220 on the shuttle valve 200 and the microprocessor.

By collecting, storing and transmitting flow condition data, such as the flow rate, volume and pressure of blood flowing through the blood vessels when the valves are closed, embodiments of the present invention enable automatic calculation and monitoring of certain significant physiological characteristics in the vicinity of the AV shunt. "Venous compliance," for example, is a measure of the tendency of the vein to resist recoil toward its original dimensions upon removal of a distending or compressing force, such as the force created by an AV shunt or AV fistula dumping blood directly into the vein without the blood first traveling through the capillaries and other smaller blood vessels. As the data describing pressure and volume changes in the area of the AV shunt are collected, stored and retrieved by embodiments of the current invention, venous compliance may be calculated using the equation $$C = \Delta V / \Delta P,$$

where $\Delta V$ is the change in volume, and $\Delta P$ is the change in pressure.

In another example, "vascular resistance" is a measure of the resistance to flow that must be overcome to push blood through the circulatory system. As the data describing pressure changes and flow rate in the blood vessels in the area of the AV shunt are collected, stored and retrieved by embodiments of the current invention, vascular resistance in the vicinity of the AV shunt may be calculated using the equation $$R = \Delta P / Q$$

where R is the vascular resistance (fluid resistance), $\Delta P$ is the pressure difference across two pressure sensors and Q is the rate of blood flow between the two sensors.

In yet another example, wall shear stress is a measure of the shear stress along the boundary of a blood vessel. Abnormal wall shear stress is associated with the development of intimal hyperplasia, which is a precursor of graft thrombosis. Thus, using velocity data collected by velocity sensors incorporated attached to the anastomotic valves in embodiments of the present invention, the wall shear stress in the blood vessel near the AV shunt may be determined according to the formula $$\tau_w = \tau(y = 0) = \mu \frac{\partial u}{\partial y}\bigg|_{y=0}.$$

where
$\mu$ is the dynamic viscosity of the blood;
u is the velocity of the blood along the boundary; and
y is the height above the boundary.

The microprocessor in embodiments of the current invention may optionally be preprogrammed to calculate and provide physiological measurements, such as venous compliance, vascular resistance and wall shear stress, based on pressure, volume, flow rate and velocity data collected by the sensors located in the anastomotic valves, thereby reducing or eliminating one or more data processing steps that would otherwise have to be performed on the data after it has been extracted from the device.

Figure 14:
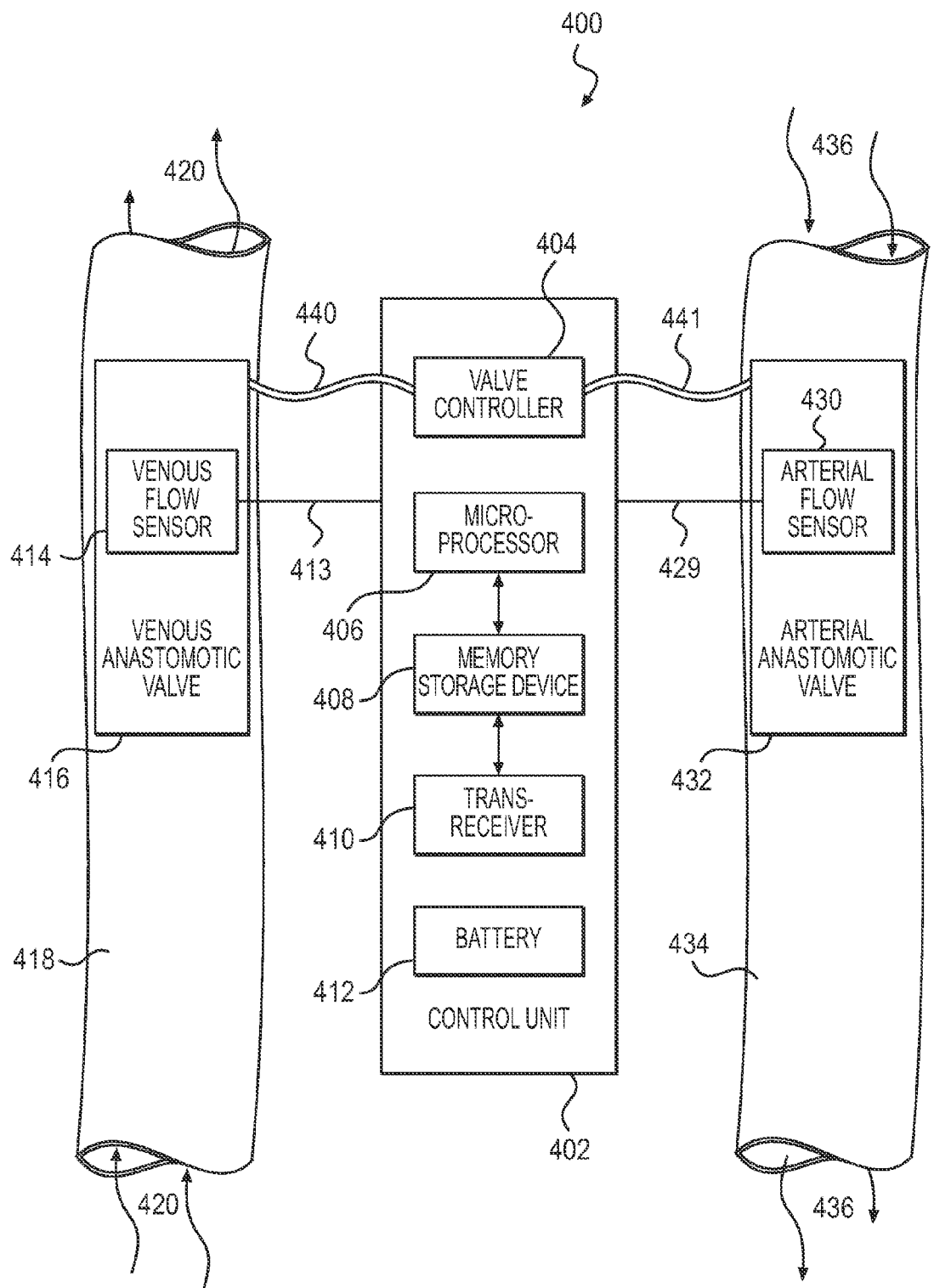
FIG. 14 shows a block diagram of an integrated surveillance system for an implantable arteriovenous shunt according to an embodiment of the invention.

FIG. 14 shows a block diagram of an integrated surveillance system 400 for an implantable arteriovenous shunt according to an embodiment of the invention. As shown in FIG. 14, the integrated surveillance system 400 includes a control unit 402, comprising a valve controller 404, a microprocessor 406, a memory storage device 408, a transceiver 410 and a battery 412. The control unit 402 is electrically coupled to a venous flow sensor 414 attached to a venous anastomotic valve 416 via an electrical lead 413. The venous anastomotic valve 416 is attached to a vein 418 in a patient's circulatory system, such that blood 420 flowing through the vein 418 will come into contact with and flow over the venous flow sensor 414 while the venous anastomotic valve 416 is in the closed position. As the blood 420 flows past the venous flow sensor 414, the venous flow sensor 414 records data describing the flow conditions for the blood 420 flowing through the vein 418 at the venous anastomotic valve 416 and transmits the data to the control unit 402 via the electrical lead 413. The data is then stored in the memory storage device 408 to be later transmitted via the transceiver 410 in response to the microprocessor 406 receiving a predetermined data extraction activation signal.

In preferred embodiments, the control unit 402 may also be electrically coupled to an arterial flow sensor 430 attached to a venous anastomotic valve 432 via an electrical lead 429. The arterial anastomotic valve 432 is attached to an artery 434 in the patient's circulatory system, such that blood 436 flowing through the artery 434 will come into contact with and flow over the arterial flow sensor 430 while the arterial anastomotic valve 432 is in the closed position. As the blood 436 flows past the arterial flow sensor 430, the arterial flow sensor 430 records data describing the flow conditions for the blood 436 flowing through the artery 434 at the arterial anastomotic valve 432 and transmits the data to the control unit 402 via the electrical lead 429. The data is then stored in the memory storage device 408 to be later transmitted via the transceiver 410 in response to the microprocessor 406 receiving a predetermined data extraction activation signal.

The valve controller 404, comprising, for example, a fluid injection port, is operable to open and close the venous and arterial anastomotic valves. In preferred embodiments, the valve controller 404 may operate to independently open and close the venous and arterial anastomotic valves by carrying a biocompatible hydraulic fluid to the venous and arterial anastomotic valves via flexible fluid tubes 440 and 441, respectively, such that the hydraulic fluid provides the mechanical force sufficient to overcome a biasing device, such as a spring, which otherwise keeps the valves closed while the patient is not currently undergoing dialysis treatment.

Although the exemplary embodiments of the invention have been disclosed above with a certain degree of particularity, it will be apparent to those skilled in the art upon consideration of this specification and practice of the invention as disclosed herein that alterations and modifications can be made without departing from the spirit or the scope of the invention.

What is claimed is:
1. A hemodialytic angioaccess device comprising:
   an arteriovenous shunt;
   an arterial anastomotic valve that connects one end of the arteriovenous shunt to an artery;
   a venous anastomotic valve that connects an opposite end of the arteriovenous shunt to a vein;
   a valve control system that is operable to independently open and close the arterial and venous anastomotic valves, wherein when the arterial and venous anastomotic valves are open blood flows through the arteriovenous shunt, and wherein when the arterial and venous anastomotic valves are closed blood does not flow through the arteriovenous shunt; and
   an integrated surveillance system that measures flow conditions in the vein while the venous anastomotic valve is closed, the integrated surveillance system including a venous flow sensor, attached to the venous anastomotic valve to collect data describing the flow conditions in the vein.

2. The hemodialytic angioaccess device of claim 1, wherein the integrated surveillance system comprises:
   a microprocessor; and
   a memory storage device;
   wherein the microprocessor is preprogrammed to cause the data describing the flow conditions in the vein to be stored in the memory storage device.

3. The hemodialytic angioaccess device of claim 2, further comprising:
   a transceiver, coupled to the microprocessor, which receives a radio frequency signal generated by an external transmitter;
   wherein, responsive to receipt of the radio frequency signal, the microprocessor will retrieve the data from the memory storage device and cause the transceiver to transmit the data to an external receiver.

4. The hemodialytic angioaccess device of claim 2, wherein the integrated surveillance system further comprises:
   an arterial flow sensor, attached to the arterial anastomotic valve, which collects data describing the flow conditions in the artery while the arterial anastomotic valve is closed.

5. The hemodialytic angioaccess device of claim 4, wherein the microprocessor is preprogrammed to cause the data describing the flow conditions in the artery to be stored in the memory storage device.

6. The hemodialytic angioaccess device of claim 4, wherein the arterial anastomotic valve comprises a shuttle valve, the shuttle valve including a valve housing; a stopper, movably disposed within the valve housing, the stopper having the arterial flow sensor attached thereto; an electrical connector on the valve housing; an electrical contact on the stopper that engages with the electrical connector when the stopper is in the closed position; and an electrical lead that carries electronic signals from the arterial flow sensor to the electrical contact.

7. The hemodialytic angioaccess device of claim 1, wherein the venous flow sensor comprises a hot-wire anemometer configured to measure forced convective heat transfer from a thermal element to the blood flowing through the vein at the closed venous anastomotic valve.

8. The hemodialytic angioaccess device of claim 1, wherein the venous flow sensor comprises a pressure sensor configured to measure pressure of the blood flowing through the vein at the closed venous anastomotic valve.

9. The hemodialytic angioaccess device of claim 1, wherein the venous flow sensor comprises a volumetric sensor configured to measure volume of blood flowing through the vein at the closed venous anastomotic valve.

10. The hemodialytic angioaccess device of claim 1, wherein the arteriovenous shunt comprises a single flexible tube.

11. The hemodialytic angioaccess device of claim 1, wherein the arteriovenous shunt comprises two or more flexible tubes.

12. The hemodialytic angioaccess device of claim 11, further comprising:
a medial flow control unit, interposed between the two or more flexible tubes; and
a memory storage device, located on the medial flow control unit, that stores flow condition measurements generated by the integrated surveillance system.

13. The hemodialytic angioaccess device of claim 1, wherein the venous anastomotic valve comprises a shuttle valve, the shuttle valve including a valve housing; a stopper, movably disposed within the valve housing, the stopper having the venous flow sensor attached thereto; an electrical connector on the valve housing; an electrical contact on the stopper that engages with the electrical connector when the stopper is in the closed position; and an electrical lead that carries electronic signals from the venous flow sensor to the electrical contact.

14. A modular hemodialytic angioaccess device, comprising:
an arteriovenous shunt having three or more conjoined pieces connected in a series, the three or more conjoined pieces comprising a first flexible tube, a second flexible tube, and a medial flow control unit piece interposed between the first flexible tube and the second flexible tube, wherein the medial flow control unit includes a memory storage device and a microprocessor;
an arterial anastomotic valve that joins the first flexible tube to an artery and permits a portion of blood flowing through the artery to flow into the arteriovenous shunt;
a venous anastomotic valve that joins the second flexible tube to a vein and permits the portion of blood flowing into the arteriovenous shunt to pass into the vein;
a valve control system that is operable to independently open and close the arterial and venous anastomotic valves, wherein when the arterial and venous anastomotic valves are open blood flows through the arteriovenous shunt, and wherein when the arterial and venous anastomotic valves are closed blood does not flow through the arteriovenous shunt;
an integrated surveillance system that measures flow conditions in the artery or the vein while the arterial anastomotic valve and the venous anastomotic valve are closed;
a venous flow sensor, attached to the venous anastomotic valve, configured to collect data describing the flow conditions in the vein;
an arterial flow sensor, attached to the arterial anastomotic valve, configured to collect data describing the flow conditions in the artery;
a microprocessor; and
a memory storage device;
wherein the microprocessor is preprogrammed to cause the data collected by the venous flow sensor to be stored in the memory storage device.

15. The modular arteriovenous shunt system of claim 14, wherein the venous flow sensor comprises a hot-wire anemometer configured to measure forced convective heat transfer from a thermal element to the blood flowing through the vein at the venous anastomotic valve.

16. The modular arteriovenous shunt system of claim 14, wherein the venous flow sensor comprises a pressure sensor configured to measure pressure of the blood flowing through the vein at the venous anastomotic valve.

17. The modular arteriovenous shunt system of claim 14, wherein the venous flow sensor comprises a volumetric sensor configured to measure volume of blood flowing through the vein at the venous anastomotic valve.

18. The modular hemodialytic angioaccess device of claim 14, further comprising:
a transceiver, coupled to the microprocessor, which receives a radio frequency signal generated by an external transmitter;
wherein, responsive to the receipt of the radio frequency signal, the microprocessor will retrieve the data from the memory storage device and cause the transceiver to transmit the data to an external receiver.

19. The modular hemodialytic angioaccess device of claim 14, wherein the integrated surveillance system includes one or more flow sensors which measure flow conditions in both the artery and the vein while the arterial anastomotic valve and the venous anastomotic valve are closed.

20. The modular hemodialytic angioaccess device of claim 14, wherein the integrated surveillance system includes one or more flow sensors which measure flow conditions in both the artery and the vein while the arterial anastomotic valve and the venous anastomotic valve are open.

21. The modular hemodialytic angioaccess device of claim 14, wherein the venous anastomotic valve comprises a shuttle valve, the shuttle valve including a valve housing; a stopper, movably disposed within the valve housing, the stopper having the venous flow sensor attached thereto; an electrical connector on the valve housing; an electrical contact on the stopper that engages with the electrical connector when the stopper is in the closed position; and an electrical lead that carries electronic signals from the venous flow sensor to the electrical contact.

22. The modular hemodialytic angioaccess device of claim 14, wherein the arterial anastomotic valve comprises a shuttle valve, the shuttle valve including a valve housing; a stopper, movably disposed within the valve housing, the stopper having the arterial flow sensor attached thereto; an electrical connector on the valve housing; an electrical contact on the stopper that engages with the electrical connector when the stopper is in the closed position; and an electrical lead that carries electronic signals from the arterial flow sensor to the electrical contact.

* * * * *